(12) United States Patent
Gabriëls et al.

(10) Patent No.: US 7,320,892 B2
(45) Date of Patent: Jan. 22, 2008

(54) NUCLEOTIDE SEQUENCES INVOLVED IN PLANT DISEASE RESISTANCE

(75) Inventors: Suzan Herma Elisabeth Johanna Gabriëls, Wageningen (NL); Jack Hubertus Vossen, Amsterdam (NL); Matthieu Henri Antoon Jozef Joosten, Wageningen (NL); Peter Jozef Marie De Wit, Rhenen (NL)

(73) Assignees: Keygene N.V., Wageningen (NL); Wageningen University, Wageningen (NL)

( * ) Notice: Subject to any disclaimer, the term of this patent is extended or adjusted under 35 U.S.C. 154(b) by 0 days.

(21) Appl. No.: 11/364,940

(22) Filed: Feb. 28, 2006

(65) Prior Publication Data

US 2006/0206958 A1 Sep. 14, 2006

Related U.S. Application Data

(63) Continuation-in-part of application No. 10/481,335, filed as application No. PCT/NL02/00417 on Jun. 24, 2002.

(30) Foreign Application Priority Data

Jun. 22, 2001 (EP) .................................. 01202420

(51) Int. Cl.
*C12N 5/04* (2006.01)
*C12N 15/82* (2006.01)
*C07H 21/04* (2006.01)

(52) U.S. Cl. ..................... 435/419; 435/468; 536/23.6
(58) Field of Classification Search .................... None
See application file for complete search history.

(56) References Cited

OTHER PUBLICATIONS van der Vossen et al. 2003 The Plant Journal 36:867-882.*
Falcon-Perez JM et al. 1999, J Biol Chem. 274:23584-90.*
Lazar et al. 1988, Mol. Cell. Biol. 8:1247-1252.*
Hill et al 1998, Biochem. Biophys. Res. Comm. 244:573-577.*
Guo et al. 2004, Proc. Natl. Acad. Sci. USA 101: 9205-9210.*
Tai et al. 1999, PNAS, 96:14153-14158.*
Logemann et al. 1989, The Plant Cell 1:151-158.*
Keller et al. 1999, The Plant Cell 11:223-235.*
Wada, Y. et al.; "Association between up-regulation of stress-responsive genes and hypomethylation of genomic DNA in tobacco plants"; 2004, *Mol Genet Genomics.*, vol. 271, No. 6, pp. 658-666.
Peart, Jack R. et al.; "NRG1, a CC-NB-LRR Protein, together with N, a TIR-NB-LRR Protein, Mediates Resistance against Tobacco Mosaic Virus"; 2005, *Current Biology*, vol. 15, pp. 968-973.
Peart, Jack R. et al.; "Supplemental Data; NRG1, a CC-NB-LRR Protein, together with N, a TIR-NB-LRR Protein, Mediates Resistance against Tobacco Mosaic Virus"; 2005, *Current Biology*, vol. 15, pp. S1-S3.

* cited by examiner

*Primary Examiner*—Elizabeth Mcelwain
*Assistant Examiner*—Li Zheng
(74) *Attorney, Agent, or Firm*—Townsend and Townsend and Crew LLP

(57) ABSTRACT

The present invention relates to methods for producing plants having enhanced disease resistance. NRC1 proteins and nucleic acid sequences encoding these are provided, as well as transgenic plants producing NRC1 proteins.

18 Claims, 6 Drawing Sheets

Fig 1

CC-domain

```
  1  MVDVGVEFLL  ENLKQLVLDN  VELIGGAKDE
 31  IENLRDDLSE  FNAFLKQAAM  VRSENPVLKE
 61  LVRSIRKVVN  RAEDAVDKFV  IEAKVHKDKG
 91  FKGVFDKPGH  YRRVRDAAVE  IKGIRDKMRE
121  IRQNKAHGLQ  ALLQDHDDSI  SRGGEERQPP
```

NB-ARC domain

```
151  VVEEDDVVGF  DDEAQTVIDR  LLEGSGDLEV
                 Kinase 1A
181  IPVVGMPGLG  KTTLATKIFK  HPKIEYEFFT
          RNBS-A
211  RLWLYVSQSY  KTRELYLNII  SKFTGNTKHC
                             Kinase 2
242  RDMSEKDLAL  KVQEILEEGG  KYLIVLDDVW
                              RNBS-B
271  STDAWDRIKI  AFPKNDKGNR  VLLTTRDHRV
           RNBS-C
301  ARYCNRSPHD  LKFLTDEESW  ILLEKRAFHK
                              GLPL
331  AKCLPELETN  GKSIARKCKG  LPLAIVVIAG
361  ALIGKSKTIK  EWEQVDQSVG  EHFINRDQPN
                             RNBS-D
391  SCDKLVRMSY  DVLPYDWKAC  FLYFGTFPRG
421  YLIPARKLIR  LWIAEGFIQY  RGDLSPECKA
                                  MHD
451  EEYLNELVNR  NLVMVMQRTV  DGQIKTCRVH
481  DMLYEFCWQE  ATTEENLFHE  VKFGGEQS
```

LRR and C terminus

```
509  VREVSTH  RRLCIHS  S-VVEFISK
531  KPSGEHV  RSFLCFS  PEKIDTPPTVSANISKAFP
564  LLRVFDT  ESIKINR  FCKEFFQ
585  ---LYHL  RYIAFSF  D-SIKVIPKH
605  VGELWNV  QTLIVNT  Q-QINLDIQAD
629  ILNMPRL  RHLLTNT  SAKLPALANPKTSKTTLVNQSLQTLSTIAPESCTEYV
680  LSRAPNL  KKLGIRG  KIAKLMEPSQSVLLNN
710  VKRLQFL  ENLKLIN  VGQIDQTQLRLPPA
738  SIFPTKL  RKLTLLD  T-WLEWDDMSV
762  LKQLENL  QVLKLKD  NAFKGENWELN
787  DGGFPFL  QVLCIER  ANLVSWNAS
810  GDHFPRL  KHLHISC  D-KLEKIPIG
833  LADICSL  QVMDLRN
847  STKSAAKSAREIQAKKNKLQPAKSQKFELSVFPPDSDVQTAS
```

NUCLEOTIDE SEQUENCES INVOLVED IN PLANT DISEASE RESISTANCE

CROSS-REFERENCES TO RELATED APPLICATIONS

The present patent application is a continuation-in-part of U.S. application Ser. No. 10/481,335, filed Jun. 17, 2004, which is a national phase application under 35 U.S.C. § 371 of PCT/NL02/00417 (published as WO03/000930), filed Jun. 24, 2002, which claims priority to EP01202420.4, filed Jun. 22, 2001, each of which is incorporated by reference its entirety for any purpose.

FIELD OF THE INVENTION

The present invention relates to transgenic plants and plant cells comprising a gene encoding an NRC1 protein (NB-LRR Required for HR-associated Cell Death 1) integrated in its genome and methods for making such plants and cells. Especially Solanaceae plants and plant parts (seeds, fruit, leaves, etc.) with enhanced disease resistance are provided. Also provided are isolated nucleic acid molecules encoding NRC1 proteins according to the invention, vectors comprising these, as well as isolated NRC1 proteins themselves. Further, plant cells and plants comprising one or more mutations in an endogenous NRC1 allele are provided, whereby the mutation(s) confer enhanced diseases resistance to the plants and plant cells.

BACKGROUND OF THE INVENTION

Active defense of plants, triggered upon recognition of an avirulence factor of a pathogen mediated by a resistance gene, follows the gene-for-gene model (Dangl and Jones, 2001, *Nature* 411, 826-833). To date, several plant resistance genes (R genes) have been cloned and based on the structure of the proteins they encode, the genes are divided into several groups (Hammond-Kosack and Jones, 1997, *Annu. Rev. Plant Physiol. Plant Molec. Biol.* 48, 575-607). Most R genes encode cytoplasmic NB-LRR proteins, containing a nucleotide binding site (NB) and leucine-rich repeats (LRR). This group consists of genes encoding CC-NB-LRR proteins, containing a coiled-coil domain and genes that encode proteins that have a domain similar to mammalian Toll and interleukin (IL) receptors, the so-called TIR-NB-LRR proteins (Hammond-Kosack and Jones, 1997, supra).

Using such specific resistance genes in breeding programs for durable resistance is problematic since pathogens easily circumvent recognition by mutations in their avirulence factors, thereby preventing induction of active defense (Westerink et al., 2004, *Mol. Microbiol.* 54, 533-545). Similarity among resistance proteins (R proteins) suggests the existence of common resistance pathways (Shirasu and Schulze-Lefert, 2000, *Plant Mol. Biol.* 44, 371-385). Therefore, identification of additional genes required for resistance not only provides information on how such signaling pathways function but might also enable us to identify genes that play a more general role in resistance. For example, by virus-induced gene silencing (VIGS) in *Nicotiana benthamiana* it was shown that SGT1 is involved in multiple defense pathways, such as N-, Rx- and Pto-mediated HR and resistance, and Cf-4- and Cf-9-mediated HR (Peart et al., 2002, *Proc. Natl. Acad. Sci. USA* 99, 10865-10869; Zhang et al., 2004, *Plant J.* 40, 213-224). SGT1 is an interactor of SKP1, which is a component of the SCF E3-ligase complex that is involved in ubiquitination of proteins, a modification which targets them for degradation (Schwechheimer and Schwager, 2004, *Plant Cell Reports* 23, 353-364). It is hypothesized that silencing an essential gene of this protein degradation system hampers the ubiquitination process, thereby inhibiting the degradation of negative regulators, which is required for defense activation (Azevedo et al., 2002, *Science* 295, 2073-2076).

In several resistance pathways MAPKs (mitogen activated protein kinases) are activated (Zhang and Klessig, 2001, *Trends Plant Sci.* 6, 520-527; Pedley and Martin, 2005, Curr. Opin. Plant Biol. 8, 541-547). In Cf-9-containing tobacco plants and cell cultures challenged with Avr9, NtWIPK (wound-induced protein kinase) and NtSIPK (salicylic acid-induced protein kinase) are activated (Romeis et al., 1999, *Plant Cell* 11, 273-287). VIGS of a NtCDPK (calcium-dependent protein kinase) in *N. benthamiana* inhibits the Cf-9/Avr9- and Cf-4/Avr4-dependent HR (Romeis et al., 2001, *EMBO J.* 20, 5556-5567) and VIGS of LeACIK1 (Avr/Cf-induced kinase 1) in tomato results in decreased *C. fulvum* resistance (Rowland et al., 2005, *Plant Cell* 17, 295-310). The activation of kinases during defense and the decreased resistance upon 'knock-down' of their encoding genes supports their function in defense activation.

Following a biased approach, 21 genes known to be involved in defense-related signaling were used for VIGS in tomato and it was found that nine of them are involved in Pto-mediated resistance. Among these are two genes encoding MAPKKs (LeMEK1 and LeMEK2) and two genes encoding MAPKs (LeNTF6 and LeWIPK) (Ekengren et al., 2003, *Plant J.* 36, 905-917). In another study, over 2400 cDNAs from a normalized library of *N. benthamiana* cDNA were cloned in a Potato Virus X-based vector and used for VIGS in *N. benthamiana*. About 3% of the cDNAs affected Pto-dependent HR upon silencing. Among these a MAP-KKKα was identified as a positive regulator of both resistance and disease (Del Pozo et al., 2004, *EMBO J.* 23, 3072-3082).

Lu et al. (2003, *EMBO J.* 22, 5690-5699) performed VIGS using 4992 cDNAs from a normalized *N. benthamiana* cDNA library cloned into a PVX vector. Of the cDNAs, 79 (1.6%) corresponded to genes required for Pto-mediated HR, whereas silencing of only six of them also impaired Pto-mediated resistance against *Pseudomonas syringae*. VIGS using a cDNA corresponding to HSP90 abolished not only Pto-mediated HR but also Pto-, Rx- and N-mediated resistance, indicating that HSP90 is required in multiple disease resistance pathways. The same set of cDNAs was also used for VIGS in N-transgenic *N. benthamiana*, after which the plants were inoculated with a GFP-tagged strain of TMV. Resistance against TMV was most significantly suppressed upon silencing using a cDNA fragment derived from a CC-NB-LRR-encoding gene, referred to as NRG1 (N requirement gene 1) (Peart et al., 2005, *Curr. Biol.* 15, 968-973). NRG1 was shown to be specifically required for N gene function, indicating that CC-NB-LRR proteins do not only act as resistance proteins involved in recognition of avirulence factors, but are also involved in the signaling pathway initiated by the TIR-NB-LRR protein N, which eventually leads to resistance (Peart et al., 2005, supra). Thus, although the tobacco NRG1 protein functions downstream of the plant's defense signaling cascade initiated by a resistance protein, it has the drawbacks that it is specifically involved in N-mediated resistance against tobacco mosaic virus (TMV) and is not a general cofactor of disease resistance (Rx- and Pto-mediated resistance against PVX and *Pseudomonas syringae* were unaffected by NRG1 silencing), whereby it may not be suitable for creating broad pathogen resistance in crops such as tomato.

Despite the increasing information about disease resistance pathways, there is still a need in identifying genes and proteins which can be used to create plants with durable, broad range disease resistance. It is an object of the invention to provide such nucleic acids, proteins and methods for creating plants, especially plants belonging to the family Solanaceae, with enhanced disease resistance.

BRIEF SUMMARY OF THE INVENTION

The present invention provides methods for producing a transgenic plant having enhanced disease resistance compared to a non-transgenic control plant. In some embodiments, the methods comprise the steps of:
(a) transforming a plant or plant cell with a nucleotide sequence encoding an NRC1 protein operably linked to a promoter active in plant cells,
(b) regenerating a plant.

In some embodiments, said nucleotide sequence is integrated into the genome of said plant.

In some embodiments, the methods further comprise:
(c) screening the regenerated plant, or a plant derived therefrom by selfing or crossing, for resistance to one or more plant pathogens and identifying a plant comprising enhanced resistance to one or more of said plant pathogens.

In some embodiments, said promoter is a pathogen inducible promoter.

In some embodiments, the NRC1 protein comprises the amino acid sequence of SEQ ID NO: 2 or SEQ ID NO: 4, or an amino acid sequence comprising at least 70% amino acid identity to SEQ ID NO: 2 over its entire length.

In some embodiments, the plant belongs to the family Solanaceae. In some embodiments, the plant is of the genus *Solanum*.

The present invention also provides transgenic plants, plant cells, seeds or fruits, obtainable by the methods described herein.

The present invention also provides plants, plant cells, seeds or fruits comprising a chimeric gene, the chimeric gene comprising a promoter active in plant cells operably linked to a nucleic acid encoding SEQ ID NO: 2 or SEQ ID NO: 4, or an amino acid sequence comprising at least 70% amino acid sequence identity to SEQ ID NO: 2 over the entire length. In some embodiments, the plant is of the genus *Solanum*.

The present invention also provides isolated proteins comprising the amino acid sequence of SEQ ID NO: 2 or SEQ ID NO: 4, or an amino acid sequence comprising at least 70% amino acid sequence identity to SEQ ID NO: 2 over the entire length.

The present invention also provides isolated nucleic acid molecules encoding a protein comprising the amino acid sequence of SEQ ID NO: 2 or SEQ ID NO: 4, or an amino acid sequence comprising at least 70% amino acid sequence identity to SEQ ID NO: 2 over the entire length.

The present invention also provides a chimeric gene comprising a promoter active in plant cells operably linked to a nucleic acid molecule according to encoding a protein comprising the amino acid sequence of SEQ ID NO: 2 or SEQ ID NO: 4, or an amino acid sequence comprising at least 70% amino acid sequence identity to SEQ ID NO: 2 over the entire length. In some embodiments, 3' untranslated nucleic acid molecule is operably linked to the chimeric gene.

The present invention also provides vectors comprising the chimeric gene described above.

GENERAL DEFINITIONS

"HR" refers to the hypersensitive response, i.e. local plant cell death, seen as either microscopic lesions (as described by Rivas and Thomas, 2005, *Ann Rev Phytopath* 43: 395-436) and/or macroscopic lesions. Hypersensitive cell death is usually associated with other plant responses, such as production of reactive oxygen species and the activation of defense related genes in cells surrounding the HR lesion.

"Plant pathogens" refer to biotic agents which are capable of causing disease on plants, such as plant pathogenic fungi, bacteria, viruses, oomycetes, mycoplasma like organisms, nematodes, white fly and aphids and the like. Generally all strains, races or pathovars of a pathogen species which are capable of causing disease on host tissue are included herein.

"Biotrophic plant pathogens" or "biotroph" refers to a pathogen that keeps the host plant cells alive and relies on living cells for growth and tissue colonization.

"Hemibiotrophic plant pathogen" or "hemibiotroph" refers to a plant pathogen which keeps the host cells alive during at least part of its life cycle.

"Necrotrophic plant pathogen" refers to a plant pathogen which actively kills plant cells upon tissue colonization, by producing toxic enzymes, proteins or metabolites that kill host cells.

"Elicitor independent HR" refers to a hypersensitive response which develops without a pathogen or a pathogen elicitor (e.g. a fungal Avr protein) being present.

When referring to plants expressing an NRC1 protein according to the invention (e.g. a constitutively active NRC1 protein) one may also distinguish between "constitutive HR", whereby reference is made to the development of HR lesions in the absence of pathogens or pathogen elicitor proteins, and "induced HR", whereby reference is made to the development of HR lesions following the presence of an inducing stimulus (e.g. following induction of the promoter which drives expression of the nucleic acid sequence encoding the NRC1 protein, or variant thereof).

"Solanaceae" refers herein to plant genera, species, and varieties thereof, belonging to the family Solanaceae. These include species belonging to the genus *Solanum* (including *Solanum lycopersicum*, which used to be known as *Lycopersicon esculentum*), *Nicotiana, Capsicum, Petunia* and other genera.

"Disease resistance" refers herein to various levels of disease resistance or tolerance of a plant, including moderate resistance and high resistance or complete resistance to one or more pathogens. It can be measured and optionally quantified by comparison of pathogen caused symptoms (such as frequency and/or size of HR lesions, fungal mycelium, etc.) relative to those seen in susceptible control plants when grown under identical disease pressure. Such disease bioassays can be carried out using known methods. Disease resistance can also be indirectly measured as higher yield of resistant plants compared to susceptible plants when grown under disease pressure.

"Enhanced disease resistance" refers to any statistically significant increase in disease resistance of a plant or plant tissue compared to a suitable control. Both a qualitative increase (e.g. from susceptible to resistant) and a quantitative increase are encompassed herein. Also encompassed is both a reduction of disease incidence (percentage of plants becoming infected) and/or of disease severity. Preferably, a plant having enhanced disease resistance to at least one pathogen is a plant comprising at least 1%, 2%, 5%, 10%, 15%, 20%, 30%, 50%, 70%, 80%, 90%, or even 100% higher levels of resistance to the pathogen than the control plant, using appropriate bioassays and/or field assays for assessing disease resistance.

"Broad spectrum" disease resistance refers to enhanced resistance against at least two, three, four, or more pathogens of different pathogen species. For example, a host plant having enhanced resistance to several biotrophic and/or hemibiotrophic and/or necrotrophic pathogen species would be considered to have broad spectrum resistance.

"Pathogen caused symptoms" include any symptoms of disease, such as mycelium growth/biomass on/in the host tissue, bacterial growth/biomass, size and/or frequency of necrotic or chlorotic lesions on plant tissue, size and/or frequency of cankers, etc.

The term "nucleic acid sequence" (or nucleic acid molecule) refers to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

"Functional", in relation to NRC1 proteins (or variants, such as orthologs or mutants, and fragments), refers to the capability to modify the (quantitative and/or qualitative) development of HR lesions and/or the level of disease resistance by modifying the expression level of the NRC1-encoding gene (e.g. by overexpression or silencing) in a plant. For example, the functionality of a putative NRC1 protein obtained from plant species X can be tested by various methods. If the protein is functional, silencing of the NRC1 gene encoding the protein in plant species X, using e.g. VIGS or gene silencing vectors, will lead to a reduction or suppression of pathogen- or elicitor induced HR lesions and/or a reduction of pathogen resistance, as shown in the Examples for tomato. Also, complementation with a functional NRC1 protein will be capable of restoring HR lesions and/or pathogen resistance. Alternatively, transient or stable (over)expression in species X of the gene encoding the NRC1 protein (optionally together with a posttranscriptional gene silencing inhibitor) will lead to the development of elicitor independent HR lesions and/or enhanced disease resistance, especially against biotrophic and/or hemibiotrophic pathogens. See also the Examples.

The term "gene" means a DNA sequence comprising a region (transcribed region), which is transcribed into an RNA molecule (e.g. an MRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites.

A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription).

"3' UTR" or "3' non-translated sequence" (also often referred to as 3' untranslated region, or 3' end) refers to the nucleic acid sequence found downstream of the coding sequence of a gene, which comprises for example a transcription termination site and (in most, but not all eukaryotic mRNAs) a polyadenylation signal (such as e.g. AAUAAA or variants thereof). After termination of transcription, the mRNA transcript may be cleaved downstream of the polyadenylation signal and a poly(A) tail may be added, which is involved in the transport of the mRNA to the cytoplasm (where translation takes place).

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). An active protein in certain embodiments refers to a protein being constitutively active. The coding sequence is preferably in sense-orientation and encodes a desired, biologically active protein or peptide, or an active peptide fragment. In gene silencing approaches, the DNA sequence is preferably present in the form of an antisense DNA or an inverted repeat DNA, comprising a short sequence of the target gene in antisense or in sense and antisense orientation. "Ectopic expression" refers to expression in a tissue in which the gene is normally not expressed.

A "transcription regulatory sequence" is herein defined as a nucleic acid sequence that is capable of regulating the rate of transcription of a (coding) sequence operably linked to the transcription regulatory sequence. A transcription regulatory sequence as herein defined will thus comprise all of the sequence elements necessary for initiation of transcription (promoter elements), for maintaining and for regulating transcription, including e.g. attenuators or enhancers. Although mostly the upstream (5') transcription regulatory sequences of a coding sequence are referred to, regulatory sequences found downstream (3') of a coding sequence are also encompassed by this definition.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells. A "promoter active in plants or plant cells" refers to the general capability of the promoter to drive transcription within a plant or plant cell. It does not make any implications about the spatiotemporal activity of the promoter.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains (for example a Coiled Coil domain (CC), a nucleotide binding domain (NB-ARC) and a Leucine Rich Repeat (LRR) region may be combined). A chimeric protein may also be a fusion protein of two or more proteins occurring in nature. The term "domain" as used herein means any part(s) or domain(s) of the protein with a specific structure or function that can be transferred to another protein for providing a new hybrid protein with at least the functional characteristic of the domain. Specific domains can also be used to identify other NRC1 proteins, such as NRC1 orthologs from other plant species.

The terms "target peptide" refers to amino acid sequences which target a protein, or protein fragment, to intracellular organelles such as plastids, preferably chloroplasts, mitochondria, or to the extracellular space or apoplast (secretion signal peptide). A nucleic acid sequence encoding a target peptide may be fused (in frame) to the nucleic acid sequence encoding the amino terminal end (N-terminal end) of the protein or protein fragment, or may be used to replace a native targeting peptide.

A "nucleic acid construct" or "vector" is herein understood to mean a man-made nucleic acid molecule resulting from the use of recombinant DNA technology and which is used to deliver exogenous DNA into a host cell. The vector backbone may for example be a binary or superbinary vector (see e.g. U.S. Pat. No. 5,591,616, US 2002138879 and WO95/06722), a co-integrate vector or a T-DNA vector, as known in the art and as described elsewhere herein, into which a chimeric gene is integrated or, if a suitable transcription regulatory sequence is already present, only a desired nucleic acid sequence (e.g. a coding sequence, an antisense or an inverted repeat sequence) is integrated downstream of the transcription regulatory sequence. Vectors usually comprise further genetic elements to facilitate their use in molecular cloning, such as e.g. selectable markers, multiple cloning sites and the like (see below).

A "host cell" or a "recombinant host cell" or "transformed cell" are terms referring to a new individual cell (or organism) arising as a result of at least one nucleic acid molecule, especially comprising a chimeric gene encoding a desired protein or a nucleic acid sequence which upon transcription yields an antisense RNA or an inverted repeat RNA (or hairpin RNA) for silencing of a target gene/gene family, having been introduced into said cell. The host cell is preferably a plant cell or a bacterial cell. The host cell may contain the nucleic acid construct as an extra-chromosomally (episomal) replicating molecule, or more preferably, comprises the chimeric gene integrated in the nuclear or plastid genome of the host cell. Throughout the text the term "host" may also refer to the host plant species which a pathogen is able to invade or infect, but this will be clear from the context. Plant species are classified as "host" or "non-host" species in relation to a pathogen. "Non-host" species are completely immune to pathogen infection of all races or strains of a pathogen, even under optimum conditions for disease development. The "host" species are also referred to as the "host range" of a pathogen and are immune to certain (but not all) races of a pathogen.

The term "selectable marker" is a term familiar to one of ordinary skill in the art and is used herein to describe any genetic entity which, when expressed, can be used to select for a cell or cells containing the selectable marker. Selectable marker gene products confer for example antibiotic resistance, or more preferably, herbicide resistance or another selectable trait such as a phenotypic trait (e.g. a change in pigmentation) or a nutritional requirements. The term "reporter" is mainly used to refer to visible markers, such as green fluorescent protein (GFP), eGFP, luciferase, GUS and the like.

The term "ortholog" of a gene or protein refers herein to the homologous gene or protein found in another species, which has the same function as the gene or protein, but (usually) diverged in sequence from the time point on when the species harbouring the genes diverged (i.e. the genes evolved from a common ancestor by speciation). Orthologs of the tomato nrc11 gene may thus be identified in other plant species based on both sequence comparisons (e.g. based on percentages sequence identity over the entire sequence or over specific domains) and functional analysis.

The terms "homologous" and "heterologous" refer to the relationship between a nucleic acid or amino acid sequence and its host cell or organism, especially in the context of transgenic organisms. A homologous sequence is thus naturally found in the host species (e.g. a tomato plant transformed with a tomato gene), while a heterologous sequence is not naturally found in the host cell (e.g. a tomato plant transformed with a sequence from potato plants). Depending on the context, the term "homolog" or "homologous" may alternatively refer to sequences which are descendent from a common ancestral sequence (e.g. they may be orthologs).

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Sequence identity" and "sequence similarity" can be determined by alignment of two peptide or two nucleotide sequences using global or local alignment algorithms. Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length, maximizing the number of matches and minimises the number of gaps. Generally, the GAP default parameters are used, with a gap creation penalty=50(nucleotides)/8(proteins) and gap extension penalty=3(nucleotides)/2(proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or EmbossWin version 2.10.0 (using the program "needle"). Alternatively percent similarity or identity may be determined by searching against databases, using algorithms such as FASTA, BLAST, etc.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

As used herein, the term "plant" includes plant cells, plant tissues or organs, plant protoplasts, plant cell tissue cultures from which plants can be regenerated, plant calli, plant cell clumps, and plant cells that are intact in plants, or parts of plants, such as embryos, pollen, ovules, fruit (e.g. harvested tomatoes), flowers, leaves, seeds, roots, root tips and the like.

BRIEF DESCRIPTION OF THE DRAWINGS

FIG. 1—Predicted Sequence of the NRC1 Protein

The predicted sequence of the NRC1 protein (SEQ ID NO:2) is displayed. The first 150 amino acid residues represent the coiled-coil (CC) domain and residues that are predicted to form the CC structure are underlined. Residues 151 to 508 comprise the nucleotide-binding (NB-ARC) domain, with the following motifs (underlined and labeled): Kinase1A (P loop), RNBS-A, Kinase 2, RNBS-B, RNBS-C, GLPL, RNBS-D and MHD. Residues 509 to 846 comprise the 13 imperfect leucine-rich repeats (LRRs); the conserved hydrophobic and proline residues are shown in bold. Below the protein sequence the LRR consensus motif is indicated: '1' indicates a conserved aliphatic residue, 'c' indicates a conserved charged residue and 'P' indicates a conserved proline residue.

Figure 2A:
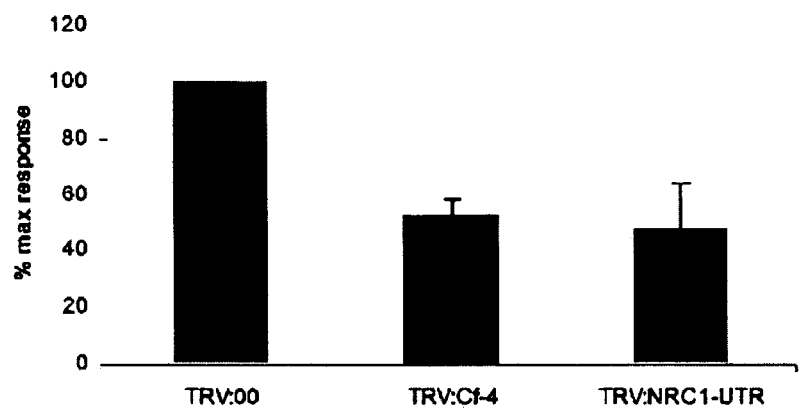

FIG. 2A—NRC1 is Required for Full Cf-4-Mediated HR of Tomato to *Cladosporium fulvum*

Cf0 tomato and Cf-4-containing tomato plants were inoculated with the indicated TRV constructs and plants were analyzed three weeks after the onset of VIGS. Leaflets of TRV-infected Cf-4-containing tomato plants were injected with Avr4 protein and examined for the development of an HR. The number of sites mounting an HR on TRV:00-infected plants was set to 100%. Each error bar represents the standard error from four independent experiments.

Figure 2B:
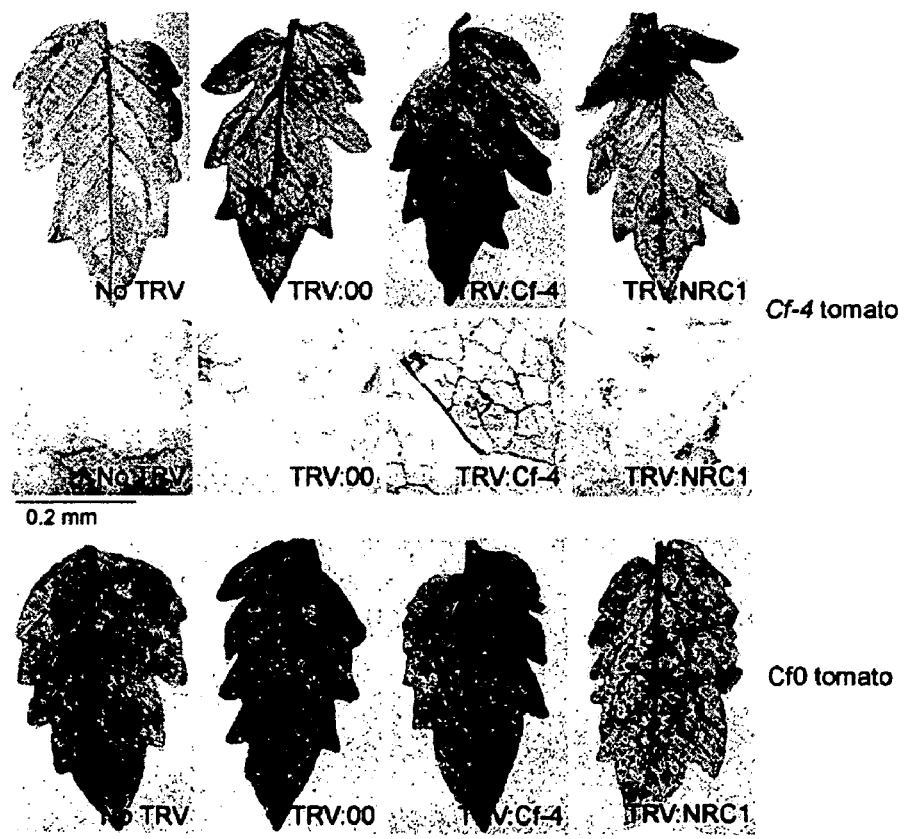

FIG. 2B—NRC1 is Required for Full Cf-4-Mediated Resistance of Tomato to *Cladosporium fulvum*

Non-TRV infected and TRV-infected Cf-4 or Cf-0 plants were inoculated with *C. fulvum*-pGPD::GUS and two weeks post inoculation colonization of the leaflets was studied with an X-gluc assay.

Figure 3:
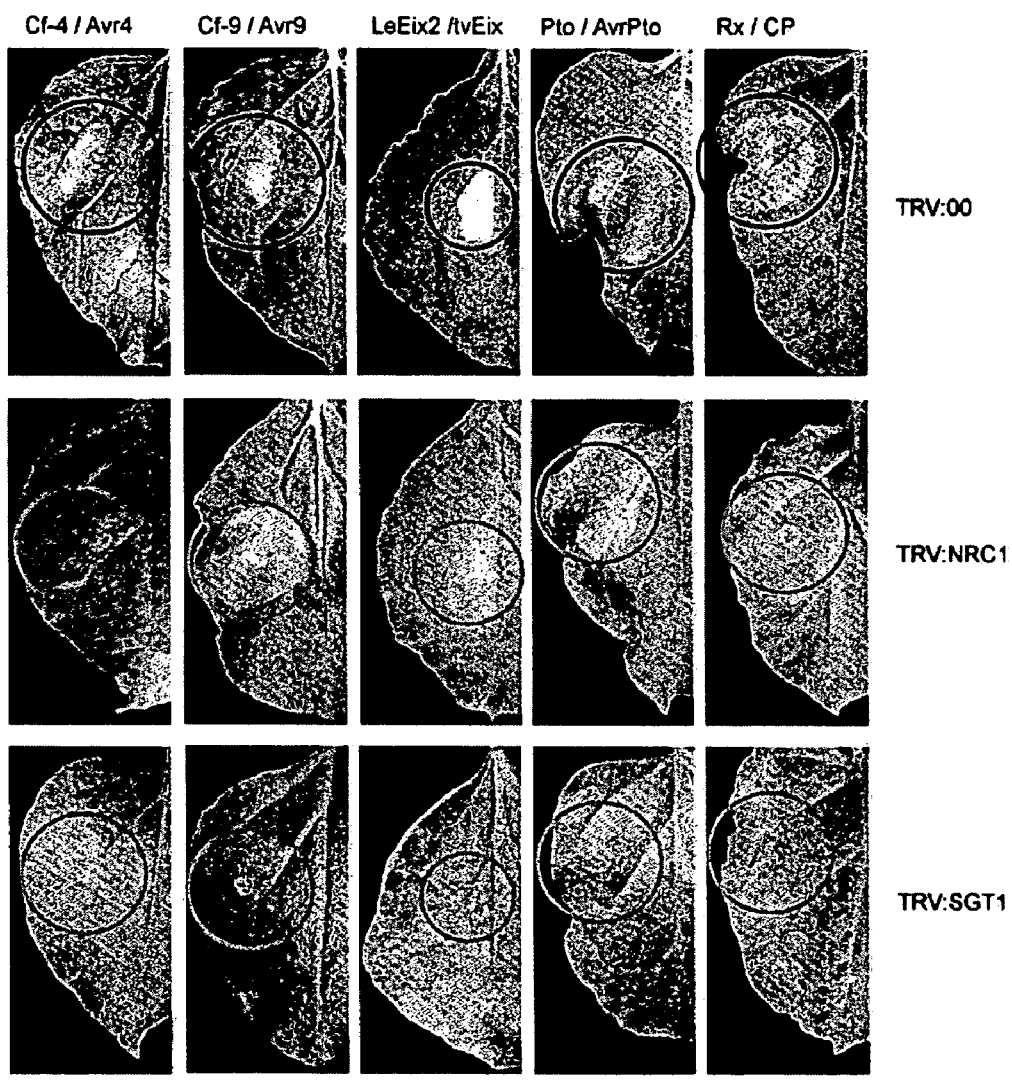

FIG. 3—Inoculation of *N. benthamiana* with TRV:NRC1 Affects Cf/Avr-, LeEix2/tvEix-, Pto/AvrPto-and Rx/CP-Induced HR

*N. benthamiana* was inoculated with TRV:00 (empty vector), TRV:NRC1 and TRV:SGT1. Three weeks later leaves were infiltrated with Agrobacteria expressing HR-inducing proteins and pictures were taken at 4 days post infiltration. First, second and third column: leaves of *N. benthamiana* expressing the Cf-4 resistance gene agroinfiltrated with Avr4 or a mix of Cf-9 and Avr9, or a mix of LeEix2 and tvEix (combined in a 1:1 ratio), respectively. Fourth column: leaves of transgenic *N. benthamiana* expressing the Pto resistance gene agroinfiltrated with AvrPto. Fifth column: leaves of transgenic *N. benthamiana* expressing the Rx resistance gene agroinfiltrated with the gene expressing the coat protein of PVX (CP). The dark circles indicate an HR, light circles indicate a compromised HR.

FIG. 4—Constitutively Active NRC1 Induces an Elicitor-Independent HR and Allows to Position NRC1 in a Cell Death Signaling Pathway

*N. benthamiana* expressing the Cf-4 resistance gene was agroinfiltrated with the indicated genes. For panels A and C, three weeks prior to agroinfiltration the plants were inoculated with the indicated TRV constructs. Dark circles indicate an HR, light circles indicate a compromised HR.

(A) Agroinfiltration of genes encoding constitutively active MAPKK and MAPK kinases. First column: agroinfiltration with the gene encoding the constitutively active kinase domain of LeMAPKKKα (MAPKKK-KD). Second column: agroinfiltration with the gene encoding a constitutively active form of LeMEK2 (MEK2DD). Two days post infiltration of MAPKKK-KD or MEK2DD expression was induced by spraying the leaves with estradiol. Pictures were taken four days post agroinfiltration.

(B) Agroinfiltration of wild-type NRC1 (wt) and mutated forms of the gene, under control of the 35S-promoter, either mixed in a 1:1 ratio with *Agrobacterium* directing expression of the gene encoding silencing suppressor p19 (left panel), or alone (right panel). NRC1$^{K191R}$ (K191R): inactive P-loop mutant of NRC1; NRC1$^{D481V}$ (D481V): constitutively active NRC1 (mutated in the MHD motif); NRC1$^{K191R/D481V}$ (K191R/D481V): double mutant of NRC1. Pictures were taken three days post agroinfiltration.

(C) Agroinfiltration of Avr4 and the gene encoding constitutively active NRC1$^{D481V}$ (D481V). Pictures were taken three days post agroinfiltration.

Figure 5:
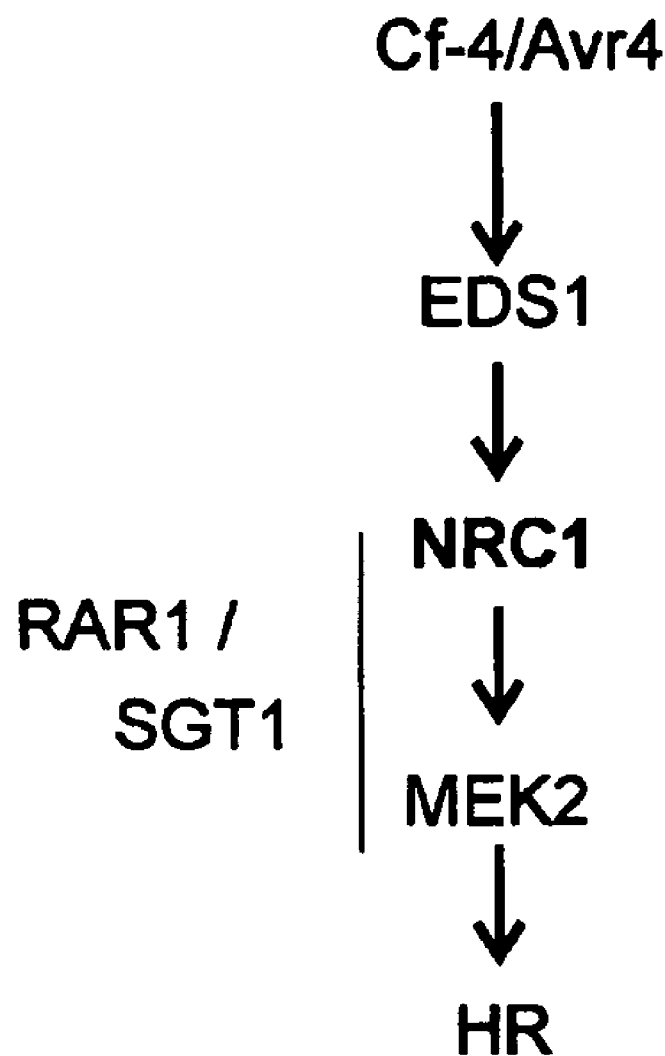

FIG. 5—Model for NRC1 Mediated Cell Death Signaling

Model based on epistasis experiments combining cell death assays and VIGS in *N. benthamiana*. Cf-4/Avr4 mediated cell death signals in an EDS1-, NRC1-, MEK2-, and SGT1/RAR1 dependent manner.

DETAILED DESCRIPTION OF THE INVENTION

The present inventors have used cDNA-AFLP analysis, in combination with VIGS (Virus Induced Gene Silencing), to identify genes involved in Cf-4/Avr4-dependent HR and disease resistance. Among the genes of which VIGS resulted in a suppression of the Avr4-induced HR, one tomato gene was identified (referred herein to as NRC1), encoding a CC-NB-LRR type resistance protein analog (herein referred to as NRC1 for NB-LRR protein Required for HR-associated Cell death 1). Silencing of NRC1 in tomato compromised not only the development of an Avr4 induced HR, but also resistance to the tomato pathogen *Cladosporium fulvum*. This indicated that the tomato Cf-4 resistance protein (an extracellular receptor like protein) requires a cytoplasmic NB-LRR protein to be functional.

Furthermore, it was surprisingly found that NRC1 is involved in multiple HR and multiple disease resistance/cell death signaling pathways, such as Cf-9/Avr-9-, LeEix2/Eix-, Pto/AvrPto- and Rx/CP-initiated HR (see Examples). Further tests are being conducted to determine whether NRC1 is also involved in other HRs, such as the Mi-mediated HR (conferring resistance to nematodes, white fly and aphid-induced HR; see U.S. Pat. No. 6,613,962 and EP0937155B1). Thus, NRC1 is involved in HR pathways triggered by both extra- and intracellular disease resistance proteins which belong to different classes: extracellular receptor like proteins (RLPs, such as Cf-4, Cf-9 and LeEix2), Ser/Thr protein kinases such as Pto and a CC-NB-LRR protein (Rx), which confer resistance to respectively fungi (*Cladosporium fulvum* and *Trichoderma viride*), a bacterium (*Pseudomonas syringae* pv tomato) or a virus (PVX).

The NRC1 protein (and the NRC1 gene encoding it) can be used to confer or enhance plant resistance against a variety of pathogens, especially biotrophic and hemibiotrophic plant pathogens, but also necrotrophic plant pathogens such as *Botrytis* species. Especially, expression of NRC1 (or variants or fragments thereof, as defined elsewhere) leads to enhanced resistance, especially against pathogens biotrophic and/or hemibiotrophic pathogens, i.e. all pathogens which obtain nutrients from living cells. Without limiting the scope of the invention, it is thought that the knock-down (gene silencing) or knock-out (e.g. by TILLING) of endogenous NRC1 genes can be used to confer or enhance resistance against necrotrophic pathogens, as the pathway leading to necrosis is affected and necrotophic pathogens require this pathway. Thus, depending on the pathogen(s) against which resistance is to be enhanced, either an increase or a decrease in NRC1 expression levels may be used to enhance resistance. Optionally both approaches may be used in one plant, e.g. under control of different promoters. For example, NRC1 can be expressed under control of a promoter induced by a (hemi)-biotrophic pathogen, to confer resistance to biotrophic and/or hemibiotrophic leaf pathogens, while at the same time endogenous NRC1 gene (or gene family) can be silenced in certain tissues, or upon induction by a necrotroph using a promoter which is inducible by necrotrophic pathogens or wounding.

It was further found that, when a constitutively active NRC1 protein (NRC1$^{D481V}$) was produced transiently in tomato, the plant tissue showed elicitor independent cell death (HR), showing that expression of a functional NRC1 protein can be used to confer or enhance disease resistance in plants.

Proteins and Nucleic Acid Sequences According to the Invention

The NRC1 protein obtained from tomato shows low sequence identity (less than 25%) to NRG1 of tobacco. NRC1 also contains a larger number of Leucine Rich Repeats (LRR) than NRG1. The protein structure of NRC1 is shown in FIG. 1 and SEQ ID NO: 2.

In one embodiment of the invention nucleic acid sequences and amino acid sequences of NRC1 proteins are provided (including orthologs), as well as methods for isolating or identifying orthologs of NRC1 in other plant species, such as other Solanaceae, preferably potato. Equally, methods for isolating or identifying other NRC1 alleles, such as alleles from other tomato species, varieties, lines or accessions are provided herein.

In one embodiment NRC1 proteins are provided. "NRC1 proteins" comprise the protein depicted in SEQ ID NO: 2 (wild type) and 4 (constitutive mutant), as well as fragments and variants thereof. Variants of NRC1 include, for example, proteins having at least 30, 35, 40, 45, 50, 55, 60, 65, 70, 75, 80, 85, 90, 95, 98, 99%, or more, amino acid sequence identity (over the entire length) to SEQ ID NO: 2 and/or 4. Amino acid sequence identity is determined by pairwise alignment using the Needleman and Wunsch algorithm and GAP default parameters as defined above. Variants of NRC1 can be obtained from various sources, such as existing sequence databases, from other plant species (especially other species of Solanaceae, such as potato) or other varieties or they can be made by de novo synthesis, mutagenesis and the like. For example, SEQ ID NO: 4, a constitutively active NRC1 mutant, which is a variant of SEQ ID NO: 2, and was made by targeted mutagenesis using overlap PCR (see Examples). The NRC1 proteins according to the invention may, thus, be isolated from natural sources, synthesized de novo by chemical synthesis (using e.g. a peptide synthesizer such as supplied by Applied Biosystems) or produced by recombinant host cells by expressing the nucleic acid sequence encoding the NRC1 protein, fragment or variant.

NRC1 variants may comprise conservative amino acid substitutions within the categories basic (e. g. Arg, His, Lys), acidic (e. g. Asp,Glu), nonpolar (e. g. Ala, Val, Trp, Leu, Ile, Pro, Met, Phe, Trp) or polar (e. g. Gly, Ser, Thr, Tyr, Cys, Asn, Gln). In addition non-conservative amino acid substitutions fall within the scope of the invention.

The functionality of any NRC1 protein, variant or fragment, can be determined using various methods. For example, transient or stable overexpression in plant cells can be used to test whether the protein has activity in planta. Functionality is preferably tested in the same plant species from which the protein is obtained. Thus, for example transient or stable expression can be used to determine whether an HR develops and/or whether resistance is enhanced, indicating functionality. Alternatively, silencing of the endogenous genes or gene family will show whether the NRC1 protein is functional. For example, VIGS can be used in a variety of Solanaceae, such as potato, tomato and tobacco (see Brigneti et al., 2004, *Plant Journal* 39: 264; Faivre-Rampant et al. *Plant Physiology* 134: 1308-1316; Baulcombe 1999, *Curr. Opinion. Plant Biol.* 2: 109-113; Lu et al. 2003, *EMBO J.* 22:5690-5699), in model organisms such as *Arabidopsis* (Turnage et al. 2002, *Plant J.* 30: 107-114), in monocots such as barley (Holzberg et al. 2002, *Plant J.* 30: 315-327). Alternatively, silencing vectors comprising sense and/or antisense fragments of an NRC1 gene can be used to transform plant cells (see below), followed by an assay to determined whether the capability to develop HR lesions and/or disease resistance is modified.

In a preferred embodiment variants of NRC1 include NRC1 proteins which are constitutively active in plant cells, such as the NRC1 protein provided in SEQ ID NO: 4, which comprises a single amino acid substitution in the MHD domain (D481V) (see FIG. 1). The constitutive activity can be tested by determining whether the protein is capable of eliciting an HR in plant tissue, in the absence of elicitor. For example, Agroinfiltration of a 35S:NRC1 construct, as described in the Examples, can be used to infiltrate leaf tissue. Other constitutively active NRC1 proteins can be made, by either random mutagenesis followed by activity testing (as described in Bendahame et al., 2002, p196) or by site directed mutagenesis of single amino acids in the MHD domain (any one of amino acids VHD or VHDM may be replaced with another amino acid), the NB-ARC domain, e.g. in the RNBS-D domain (amino acids FLYFGTFPRGY), or one of the 13 LRR domains (see FIG. 1). Alternatively, nucleic acid sequences encoding constitutively active NRC1 proteins can be obtained from plants, for example by mutagenizing seeds and screening these for the presence of a spontaneous lesion phenotype (for example microscopic lesions), see e.g. Sharino et al. (2002, *The Plant Cell* 14: 3149-3162) and further below.

In one embodiment also chimeric NRC1 proteins are provided. Such proteins comprise at least a CC domain, a NB-ARC domain and preferably at least 13 LRRs. A CC-, NB-ARC- and LRR-domain preferably refers to amino acid motifs comprising at least 30, 40, 50, 60, 70, 80, 90, 95, 98, 99%, or more, amino acid sequence identity to amino acids 1-150, to amino acids 151-508, or to amino acids 509-846 of SEQ ID NO: 2 respectively. Domains may thus be exchanged (domain swapping) between NRC1 proteins or between NRC1 proteins and other CC-NB-LRR or TIR-NB-LRR proteins, as long as the functionality of the resulting chimeric protein is essentially similar to that of NRC1, or preferably to NRC1$^{D481V}$. Most preferably, the chimeric protein retains the ability to confer or enhance disease resistance when it is produced by recombinant plant cells, as described below.

"Fragments" of NRC1 proteins and of variants of NRC1 proteins, as described above, comprise fragments of 100, 150, 200, 300, 400, 500, 600, 700, 800, 850, 855 contiguous amino acids or more. Preferably, such fragments are functional in plant tissue, i.e. they are capable of conferring or enhancing pathogen resistance when produced in plant cells. Fragments may also be used to make chimeric proteins, as described above.

In another embodiment isolated nucleic acid sequences encoding any of the above proteins, variants or fragments are provided, such as cDNA, genomic DNA and RNA sequences. Due to the degeneracy of the genetic code various nucleic acid sequences may encode the same amino acid sequence. Any nucleic acid sequence encoding NRC1 proteins or variants are herein referred to as "NRC1". The nucleic acid sequences provided include naturally occurring, artificial or synthetic nucleic acid sequences. Examples of nucleic acid sequences encoding NRC1 proteins are provided for in SEQ ID NO: 1 and 3. It is understood that when sequences are depicted in as DNA sequences while RNA is referred to, the actual base sequence of the RNA molecule is identical with the difference that thymine (T) is replace by uracil (U).

Also included are variants and fragments of NRC1 nucleic acid sequences, such as nucleic acid sequences hybridizing to NRC1 nucleic acid sequences under stringent hybridization conditions as defined. Variants of NRC1 nucleic acid sequences also include nucleic acid sequences which have a sequence identity to SEQ ID NO: 1 or 3 (over the entire length) of at least 50% or more, preferably at least 55%, 60%, 70%, 80%, 90%, 95%, 99%, 99.5%, 99.8% or more. In a preferred embodiment, variants of NRC1 encode constitutively active NRC1 proteins as described. It is clear that many methods can be used to identify, synthesise or isolate variants or fragments of NRC1 nucleic acid sequences, such as nucleic acid hybridization, PCR technology, in silico analysis and nucleic acid synthesis, and the like.

The nucleic acid sequence, particularly DNA sequence, encoding the NRC1 proteins of this invention can be inserted in expression vectors to produce high amounts of NRC1 proteins (or e.g. chimeric NRC1 proteins), as described below. For optimal expression in a host the NRC1 DNA sequences can be codon-optimized by adapting the codon usage to that most preferred in plant genes, particularly to genes native to the plant genus or species of interest (Bennetzen & Hall, 1982, *J. Biol. Chem.* 257, 3026-3031; Itakura et al., 1977 *Science* 198, 1056-1063.) using available codon usage tables (e. g. more adapted towards expression in cotton, soybean corn or rice). Codon usage tables for various plant species are published for example by Ikemura (1993, In "Plant Molecular Biology Labfax", Croy, ed., Bios Scientific Publishers Ltd.) and Nakamura et al. (2000, *Nucl. Acids Res.* 28, 292.) and in the major DNA sequence databases (e.g. EMBL at Heidelberg, Germany). Accordingly, synthetic DNA sequences can be constructed so that the same or substantially the same proteins are produced. Several techniques for modifying the codon usage to that preferred by the host cells can be found in patent and scientific literature. The exact method of codon usage modification is not critical for this invention.

Small modifications to a DNA sequence such as described above can be routinely made, i.e., by PCR-mediated mutagenesis (Ho et al., 1989, *Gene* 77, 51-59., White et al., 1989, *Trends In genet.* 5, 185-189). More profound modifications to a DNA sequence can be routinely done by de novo DNA synthesis of a desired coding region using available techniques.

Also, the NRC1 nucleic acid sequences can be modified so that the N-terminus of the NRC1 protein has an optimum translation initiation context, by adding or deleting one or more amino acids at the N-terminal end of the protein. Often it is preferred that the proteins of the invention to be expressed in plants cells start with a Met-Asp or Met-Ala dipeptide for optimal translation initiation. An Asp or Ala codon may thus be inserted following the existing Met, or the second codon, Val, can be replaced by a codon for Asp (GAT or GAC) or Ala (GCT, GCC, GCA or GCG). The DNA sequences may also be modified to remove illegitimate splice sites.

"Fragments" of NRC1 nucleic acid sequences include fragments of at least 10, 12, 15, 16, 18, 20, 30, 40, 50, 100, 200, 500, 1000, 1500, 2000 or more consecutive nucleotides of SEQ ID NO: 1 or 3, or of variants of SEQ ID NO: 1 or 3. Short fragments can for example be used as PCR primers or hybridization probes.

In another embodiment of the invention PCR primers and/or probes and kits for detecting the NRC1 DNA or RNA sequences are provided. Degenerate or specific PCR primer pairs to amplify NRC1 DNA from samples can be synthesized based on SEQ ID NO: 1 or 3 (or variants thereof) as known in the art (see Dieffenbach and Dveksler (1995) PCR Primer: A Laboratory Manual, Cold Spring Harbor Laboratory Press, and McPherson at al. (2000) PCR-Basics: From Background to Bench, First Edition, Springer Verlag, Germany). For example, any stretch of 9, 10, 11, 12, 13, 14, 15, 16, 18 or more contiguous nucleotides of SEQ ID NO: 1 or 3 (or the complement strand) may be used as primer or probe. Likewise, DNA fragments of SEQ ID NO: 1 or 3 (or variants thereof) can be used as hybridization probes. An NRC1 detection kit may comprise either NRC1 specific primers and/or NRC1 specific probes, and an associated protocol to use the primers or probe to detect NRC1 DNA in a sample. Such a detection kit may, for example, be used to determine, whether a plant has been transformed with an NRC1 gene (or part thereof) of the invention. Because of the degeneracy of the genetic code, some amino acid codons can be replaced by others without changing the amino acid sequence of the protein.

In yet another embodiment a method for identifying and using orthologs or alleles of the tomato NRC1 gene (SEQ ID NO: 1 and 3) is provided. The method comprises the steps of:

a) obtaining or identifying a nucleic acid sequence comprising at least 70% nucleic acid identity to SEQ ID NO: 1 and/or 3 (or a higher percentage sequence identity, as indicated above), b) optionally modifying the nucleic acid sequence to encode a constitutively active NRC1 protein, and c) using the nucleic acid sequence of a) to generate expression and/or silencing vectors, or using the nucleic acid sequence of b) to generate expression vectors, d) using one or more vectors of c) to transform a plant or plant cell(s), preferably of the plant species from which the nucleic acid was obtained, e) analysing the capability of the transformed plant/plant tissue to develop HR lesions (i.e. the HR lesion phenotype, which can optionally be quantified) and/or the disease resistance of the transformants in order to determine or verify the gene function in planta and/or to generate transgenic plants having enhanced disease resistance;

f) optionally selecting those alleles or orthologs for further use which confer enhanced disease resistance to the transgenic plant but which, upon expression, confer a weak HR phenotype (i.e. cause no or a reduced HR lesion phenotype).

Thus, NRC1 alleles or orthologs, which upon expression in plants result in fewer and/or smaller HR lesions than seen upon expression of SEQ ID NO: 1 or 3, or upon expression of the wild type NRC1 allele obtained from the host species to be transformed, can be identified using this method. Most preferably, NRC1 alleles or orthologs are identified which cause no HR lesions, or at least no macroscopically visible HR lesions, upon expression, but which still confer enhanced disease resistance.

The HR phenotype of different NRC1 alleles and/or orthologs can be compared by making expression vectors using the same promoters, transforming a host plant with these, and by comparing the HR lesion phenotype between these transgenic plants. When different alleles are compared in transgenic Solanaceae plants (e.g. under control of a constitutive or inducible promoter), the HR lesion phenotype of transformants expressing SEQ ID NO: 1 or 3 is preferably used as reference. Alternatively, the wild type allele obtained from the host species to be transformed can be used as reference. Those alleles which provide fewer and/or smaller HR lesions compared to SEQ ID NO: 1 or 3, or fewer and/or smaller HR lesions than caused by expression of the wild type allele obtained from the species transformed, can then be selected for further use. For example transgenic plants expressing these can be made as described below.

Especially alleles from tomato and orthologs from potato may be obtained or identified using e.g. NRC1-specific PCR primers or probes, or bioinformatics analysis in silico. Also genetic mapping may be used to map the NRC1 locus in the plant (e.g. tomato or potato) genome, whereby sequences may be obtained by linking the genomic map to existing genome sequencing databases (e.g. developed in the tomato sequencing project). Such alleles and/or orthologs may be especially suitable for generating plants with enhanced disease resistance.

When potato orthologs of NRC1 are identified in the above method, these orthologs (or variants of these orthologs) are preferably used to generate plants having enhanced resistance to *Phytophthora infestans*.

Chimeric Genes, Expression Vectors and Recombinant Organisms According to the Invention In one embodiment of the invention nucleic acid sequences encoding NRC1 proteins (including variants or fragments), as described above, are used to make chimeric genes, and vectors comprising these for transfer of the chimeric gene into a host cell and production of the NRC1 protein(s) in host cells, such as cells, tissues, organs or organisms derived from transformed cell(s). Vectors for the production of NRC1 protein (or protein fragments or variants) in plant cells are herein referred to as i.e. "expression vectors". Host cells are preferably plant cells and, but microbial hosts (bacteria, e.g. *Agrobacterium*, yeast, fungi, etc.) are also envisaged.

Any plant may be a suitable host, such as monocotyledonous plants or dicotyledonous plants, but most preferably the host plant belongs to the family Solanaceae. For example, the plant belongs to the genus *Solanum* (including *Lycopersicon*), *Nicotiana*, *Capsicum*, *Petunia* and other genera. The following host species may suitably be used: Tobacco (*Nicotiana* species, e.g. *N. benthamiana*, *N. plumbaginifolia*, *N. tabacum*, etc.), vegetable species, such as tomato (*L. esculentum*, syn. *Solanum lycopersicum*) such as e.g. cherry tomato, var. *cerasiforme* or currant tomato, var. *pimpinellifolium*) or tree tomato (*S. betaceum*, syn. *Cyphomandra betaceae*), potato (*Solanum tuberosum*), eggplant (*Solanum melongena*), pepino (*Solanum muricatum*), cocona (*Solanum sessiliflorum*) and naranjilla (*Solanum quitoense*), peppers (*Capsicum annuum, Capsicumfrutescens, Capsicum baccatum*), ornamental species (e.g. *Petunia hybrida, Petunia axillaries, P. integrifolia*).

Alternatively, the plant may belong to any other family, such as to the Cucurbitaceae or Gramineae. Suitable host plants include for example maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc), sunflower (*Helianthus annus*), safflower, yam, cassava, alfalfa (*Medicago sativa*), rice (*Oryza* species, e.g. *O. sativa indica* cultivar-group or japonica cultivar-group), forage grasses, pearl millet (*Pennisetum* spp. e.g. *P. glaucum*), tree species (*Pinus*, poplar, fir, plantain, etc), tea, coffea, oil palm, coconut, vegetable species, such as pea, zucchini, beans (e.g. *Phaseolus* species), cucumber, artichoke, asparagus, broccoli, garlic, leek, lettuce, onion, radish, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. Rose, Petunia, Chrysanthemum, Lily, Gerbera species), herbs (mint, parsley, basil, thyme, etc.), woody trees (e.g. species of Populus, Salix, Quercus, Eucalyptus), fibre species e.g. flax (*Linum usitatissimum*) and hemp (*Cannabis sativa*), or model organisms, such as *Arabidopsis thaliana*.

Preferred hosts are "crop plants", i.e. plant species which is cultivated and bred by humans. A crop plant may be cultivated for food purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork and the like.

The construction of chimeric genes and vectors for, preferably stable, introduction of NRC1 protein encoding nucleic acid sequences into the genome of host cells is generally known in the art. To generate a chimeric gene the nucleic acid sequence encoding a NRC1 protein (or variant or fragment) is operably linked to a promoter sequence, suitable for expression in the host cells, using standard molecular biology techniques. The promoter sequence may already be present in a vector so that the NRC1 nucleic sequence is simply inserted into the vector downstream of the promoter sequence. The vector is then used to transform the host cells and the chimeric gene is inserted in the nuclear genome or into the plastid, mitochondrial or chloroplast genome and expressed there using a suitable promoter (e.g., Mc Bride et al., 1995 *Bio/Technology* 13, 362; U.S. Pat. No. 5,693,507). In one embodiment a chimeric gene comprises a suitable promoter for expression in plant cells or microbial cells (e.g. bacteria), operably linked thereto a nucleic acid sequence encoding a NRC1 protein according to the invention, optionally followed by a 3' nontranslated nucleic acid sequence.

The NRC1 nucleic acid sequence, preferably the NRC1 chimeric gene, encoding an functional NRC1 protein (or in certain embodiments a constitutively active NRC1 protein), can be stably inserted in a conventional manner into the nuclear genome of a single plant cell, and the so-transformed plant cell can be used in a conventional manner to produce a transformed plant that has an altered phenotype due to the presence of the NRC1 protein in certain cells at a certain time. In this regard, a T-DNA vector, comprising a nucleic acid sequence encoding a NRC1 protein, in *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO84/02913 and published European Patent application EP 0 242 246 and in Gould et al. (1991, *Plant Physiol.* 95, 426-434). The construction of a T-DNA vector for *Agrobacterium* mediated plant transformation is well known in the art. The T-DNA vector may be either a binary vector as described in EP 0 120 561 and EP 0 120 515 or a co-integrate vector which can integrate into the *Agrobacterium* Ti-plasmid by homologous recombination, as described in EP 0 116 718.

Preferred T-DNA vectors each contain a promoter operably linked to NRC1 encoding nucleic acid sequence (e.g. encoding SEQ ID NO: 2 or SEQ ID NO: 4) between T-DNA border sequences, or at least located to the left of the right border sequence. Border sequences are described in Gielen et al. (1984, *EMBO J* 3,835-845). Of course, other types of vectors can be used to transform the plant cell, using procedures such as direct gene transfer (as described, for example in EP 0 223 247), pollen mediated transformation (as described, for example in EP 0 270 356 and WO85/01856), protoplast transformation as, for example, described in U.S. Pat. No. 4,684,611, plant RNA virus-mediated transformation (as described, for example in EP 0 067 553 and U.S. Pat. No. 4,407,956), liposome-mediated transformation (as described, for example in U.S. Pat. No. 4,536, 475), and other methods. For tomato or tobacco transformation see also An G. et al., 1986, *Plant Physiol.* 81: 301-305; Horsch R. B. et al., 1988, *In: Plant Molecular Biology Manual* A5, Dordrecht, Netherlands, Kluwer Academic Publishers. pp 1-9; Koornneef M. et al., 1986, In: Nevins D. J. and R. A. Jones, eds. *Tomato Biotechnology*, New York, N.Y., USA, Alan R. Liss, Inc. pp 169-178). For potato transformation see e.g. Sherman and Bevan (1988, *Plant Cell Rep.* 7: 13-16).

Likewise, selection and regeneration of transformed plants from transformed cells is well known in the art. Obviously, for different species and even for different varieties or cultivars of a single species, protocols are specifically adapted for regenerating transformants at high frequency.

Besides transformation of the nuclear genome, also transformation of the plastid genome, preferably chloroplast genome, is included in the invention. One advantage of plastid genome transformation is that the risk of spread of the transgene(s) can be reduced. Plastid genome transformation can be carried out as known in the art, see e.g. Sidorov V A et al. 1999, *Plant J.* 19: 209-216 or Lutz K A et al. 2004, *Plant J.* 37(6):906-13.

The resulting transformed plant can be used in a conventional plant breeding scheme to produce more transformed plants containing the transgene. Single copy transformants can be selected, using e.g. Southern Blot analysis or PCR based methods or the Invader® Technology assay (Third Wave Technologies, Inc.). Transformed cells and plants can easily be distinguished from non-transformed ones by the presence of the chimeric gene. The sequences of the plant DNA flanking the insertion site of the transgene can also be sequenced, whereby an "Event specific" detection method can be developed, for routine use. See for example WO01141558, which describes elite event detection kits (such as PCR detection kits) based for example on the integrated sequence and the flanking (genomic) sequence.

The NRC1 nucleic acid sequence is inserted in a plant cell genome so that the inserted coding sequence is downstream (i.e. 3') of, and under the control of, a promoter which can direct the expression in the plant cell. This is preferably accomplished by inserting the chimeric gene in the plant cell genome, particularly in the nuclear or plastid (e. g. chloroplast) genome.

As the constitutive production of the NRC1 protein may leads to the induction of cell death (e.g. microscopic lesions and/or macroscopic lesions) and/or may lower yield (see e.g. Rizhsky and Mittler, *Plant Mol Biol,* 2001 46: 313-23), it is in one embodiment preferred to use a promoter whose activity is inducible. Examples of inducible promoters are wound-inducible promoters, such as the MPI promoter described by Cordera et al. (1994, *The Plant Journal* 6, 141), which is induced by wounding (such as caused by insect or physical wounding), or the COMPTII promoter (WO0056897) or the PR1 promoter described in U.S. Pat. No. 6,031,151. Alternatively the promoter may be inducible by a chemical, such as dexamethasone as described by Aoyama and Chua (1997, *Plant Journal* 11: 605-612) and in U.S. Pat. No. 6,063,985 or by tetracycline (TOPFREE or TOP 10 promoter, see Gatz, 1997, *Annu Rev Plant Physiol Plant Mol Biol.* 48: 89-108 and Love et al. 2000, Plant J. 21: 579-88). Other inducible promoters are for example inducible by a change in temperature, such as the heat shock promoter described in U.S. Pat. No. 5,447,858, by anaerobic conditions (e.g. the maize ADH1S promoter), by light (U.S. Pat. No. 6,455,760), by pathogens (e.g. the gst1 promoter of EP759085 or the vst1 promoter of EP309862) or by senescence (SAG12 and SAG13, see U.S. Pat. No. 5,689,042). Obviously, there are a range of other promoters available.

In one embodiment preferably, a pathogen inducible promoter is used, as thereby the NRC1 protein (or variant or fragment) will only be produced following pathogen attack of the plant tissue. Especially, promoters of genes which are upregulated quickly after pathogen attack are desired. Pathogen inducible promoters include, for example, the hsr203J, str246C and sgd24 promoters from tobacco, EAS4 promoter described by Yin et al. (1997, *Plant Physiology* 115(2):437-51), the tap1 or tap2 promoter (Mohan et al., 1993, *Plant Mol Biol.* 1993 22 :475-90), the gst1 promoter or variants thereof (Martini et al. 1993, *Mol. Gen. Gen.* 236, 179-186; Hennin C., 1997, Afstudeerwerk, Faculteit Landbouwkundige en Toegepaste Biologische Wetenschappen, University of Gent, Belgium), the WRKY promoters (Eulgem et al., *EMBO J.,* 1999, 18(17):4689-99 and chimeric promoters described in WO0029592). Promoters inducible by a particular plant pathogen may also be identified using known methods, such as cDNA-AFLP®.

Preferably, the promoter is inducible by a number of pathogens, i.e. it is inducible by a broad range of pathogens of the host plant. For each particular host plant species, a different promoter may be most suitable. For example, when tomato is used as a host, the promoter is preferably induced upon at least one, but preferably more than one tomato pathogen. Especially, a promoter which is inducible by one or more fungal plant pathogens and/or bacterial plant pathogens (especially by one or more biotrophic and/or hemibiotrophic plant pathogens) is preferred.

Detailed descriptions of plant pathogens, the disease symptoms caused by them and their life cycles can be found for each plant species. For example, tomato pathogens are described in "Compendium of Tomato Diseases", Editors Jones, Jones, Stall and Zitter, ISBN 0-89054-120-5, APS Press (on the world wide web at shopapspress/org). Potato pathogens are described in "Compendium of Potato Disease", 2$^{nd}$ edition, Editors Stevenson, Franc and Weingartner, APS Press, ISBN 0-89054-275-9.

Pathogens of tomato include, for example, the following fungal and bacterial species and viruses (non-limiting): *Botrytis cinerea* (fungus/necrotroph); *Colletotrichum coccodes* (fungus/necrotroph); *Alternaria alternata* (fungus); *Alternaria solani* (fungus/necrotroph); *Stemphylium solani; Phytophthora infestans* (oomycte/hemibiotroph); *Septoria lycopersici; Cladosporium fulvum,* (fungus/hemibiotroph); *Phytophthora parasitica; Oidium lycopersicum* (biotroph); *Fusarium oxysporum; Sclerotium rolfsii; Pythium; Rhizoctonia* (fungus/necrotroph); *Corynebacterium michiganense* (bacterium); *Pseudomonas syringae* pv tomato or pv *syringae* (bacterium/biotroph); *Pseudomonas solanacearum; Pseudomonas corrugate; Clavibacter Xanthomonas campestris* (bacterium/biotroph); *Verticillium* (fungus), tomato spotted wilt virus (TSWV); Tobacco or tomato mosaic viruses (TobMV, TomMV).

Pathogens of potato include, for example, various fungi, bacteria, nematodes and viruses, such as: *Phytophthora infestans* (oomycte/hemibiotroph), nematodes (biotrophic); *Erwinia carotovora* (bacterium); *Colletotrichum coccodes* (fungus); *Rhizoctonia solani* (fungus/necrotroph); *Verticillium dahliae* (fungus); *Streptomyces scabies; Alternaria solani* (fungus/necrotroph); *Pythium; Spongospora subterranean;* PVX and PVY; Potato Leafroll Virus (PLRV); etc.

See also on the world wide web at apsnet.org/online/common/toc.asp for plant diseases of various plant species. Thus, in one embodiment the promoter is preferably inducible by one or more of the above pathogens, most preferably at least by one or more of the above biotrophic and/or hemibiotrophic pathogens.

Alternatively, a host plant may comprise various NRC1 transgenes, each under control of a different pathogen inducible promoter, to ensure that NRC1 protein is produced following attack by a variety of pathogens. For example, for transformation of tomato, one promoter may be inducible by *Phytophthora* and one by *Cladosporium.*

The word "inducible" does not necessarily require that the promoter is completely inactive in the absence of the inducer stimulus. A low level non-specific activity may be present, as long as this does not result in severe yield or quality penalty of the plants. Inducible, thus, preferably refers to an increase in activity of the promoter, resulting in an increase in transcription of the downstream NRC1 coding region following contact with the inducer.

The most preferred combination herein is the use of a pathogen inducible promoter, operably linked to an NRC1 nucleic acid sequence which encodes a constitutively active NRC1 protein, as described above. In this case upon pathogen attack the constitutively active NRC1 will be expressed resulting in a local HR (restricted to the site of pathogen attack) preventing further growth of any (hemi)-biotrophic pathogen.

In another embodiment constitutive promoters may be used, such as the strong constitutive 35S promoters or enhanced 35S promoters (the "35S promoters") of the cauliflower mosaic virus (CaMV) of isolates CM 1841 (Gardner et al., 1981, *Nucleic Acids Research* 9, 2871-2887), CabbB-S (Franck et al., 1980, *Cell* 21, 285-294) and CabbB-JI (Hull and Howell, 1987, *Virology* 86, 482-493); the 35S promoter described by Odell et al. (1985, *Nature* 313, 810-812) or in U.S. Pat. No. 5,164,316, promoters from the ubiquitin family (e.g. the maize ubiquitin promoter of Christensen et al., 1992, *Plant Mol. Biol.* 18, 675-689, EP 0 342 926, see also Comejo et al. 1993, *Plant Mol. Biol.* 23, 567-581), the gos2 promoter (de Pater et al., 1992 *Plant J.* 2, 834-844), the emu promoter (Last et al., 1990, *Theor. Appl. Genet.* 81, 581-588), Arabidopsis actin promoters such as the promoter described by An et al. (1996, *Plant J.* 10, 107.), rice actin promoters such as the promoter described by Zhang et al.(1991, *The Plant Cell* 3, 1155-1165) and the promoter described in U.S. Pat. No. 5,641,876 or the rice actin 2 promoter as described in WO070067; promoters of the Cassava vein mosaic virus (WO 97/48819, Verdaguer et al. 1998, *Plant Mol. Biol.* 37, 1055-1067), the pPLEX series of promoters from Subterranean Clover Stunt Virus (WO 96/06932, particularly the S7 promoter), a alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., 1984, *EMBO J* 3, 2723-2730), the Figwort Mosaic Virus promoter described in U.S. Pat. No. 6,051,753 and in EP426641, histone gene promoters, such as the Ph4a748 promoter from Arabidopsis (PMB 8: 179-191), or others. In a preferred embodiment the AA6 promoters, as described in PCT/NL2005/050083 (filed 16 Dec. 2005) are used.

Alternatively, a promoter can be utilized which is not constitutive but rather is specific for one or more tissues or organs of the plant (tissue preferred/tissue specific, including developmentally regulated promoters), for example leaf preferred, epidermis preferred, root preferred, flower tissue e.g. tapetum or anther preferred, seed preferred, pod preferred, etc.), whereby the NRC1 gene is expressed only in cells of the specific tissue(s) or organ(s) and/or only during a certain developmental stage. For example, the NRC1 gene(s) can be selectively expressed in the leaves of a plant by placing the coding sequence under the control of a light-inducible promoter such as the promoter of the ribulose-1, 5-bisphosphate carboxylase small subunit gene of the plant itself or of another plant, such as pea, as disclosed in U.S. Pat. No. 5,254,799 or *Arabidopsis* as disclosed in U.S. Pat. No. 5,034,322.

In one embodiment the promoter of the endogenous NRC1 gene is used. For example, the promoter of the tomato NRC1 gene may be isolated and operably linked to the coding region encoding NRC1 protein of SEQ ID NO: 2 or 4. The NRC1 promoter (the upstream transcription regulatory region of SEQ ID NO: 1 and 3) can be isolated from tomato plants using known methods, such as TAIL-PCR (Liu et al. 1995, *Genomics* 25(3):674-81; Liu et al. 2005, *Methods Mol Biol.* 286:341-8), Linker-PCR, or Inverse PCR (IPCR).

The NRC1 coding sequence is preferably inserted into the plant genome so that the coding sequence is upstream (i.e. 5') of suitable 3' end nontranslated region ("3'end" or 3'UTR). Suitable 3'ends include those of the CaMV 35S gene ("3' 35S"), the nopaline synthase gene ("3' nos") (Depicker et al., 1982 *J. Molec. Appl. Genetics* 1, 561-573.), the octopine synthase gene ("3'ocs") (Gielen et al., 1984, *EMBO J.* 3, 835-845) and the T-DNA gene 7 ("3' gene 7") (Velten and Schell, 1985, *Nucleic Acids Research* 13, 6981-6998), which act as 3'-untranslated DNA sequences in transformed plant cells, and others. In one embodiment the 3'UTR of the tomato NRC1 gene is used, as shown in SEQ ID NO: 3, from nucleotide 2748 to nucleotide 3168, and as shown in SEQ ID NO: 5. The NRC1 3'UTR is also an embodiment in itself herein, as it may also be used as 3'UTR in combination with other coding regions. Equally, any variant or fragment of SEQ ID NO: 5 is provided. A variant of SEQ ID NO: 5 includes nucleic acid sequences comprising at least 40, 50, 60, 70, 80, 90, 95, 98, 99% or more nucleic acid sequence identity to SEQ ID NO: 5 (as determined using the Needleman and Wunsch algorithm and the GAP penalties as defined above). Fragments include any nucleotide sequences comprising at least 30, 50, 100, 150, 200, 300, 400 or more consecutive nucleotides of SEQ ID NO: 5, or of a variant of SEQ ID NO: 5.

Introduction of the T-DNA vector into *Agrobacterium* can be carried out using known methods, such as electroporation or triparental mating.

A NRC1 encoding nucleic acid sequence can optionally be inserted in the plant genome as a hybrid gene sequence whereby the NRC1 sequence is linked in-frame to a (U.S. Pat. No. 5,254,799; Vaeck et al., 1987, *Nature* 328, 33-37) gene encoding a selectable or scorable marker, such as for example the neo (or nptII) gene (EP 0 242 236) encoding kanamycin resistance, so that the plant expresses a fusion protein which is easily detectable.

All or part of a NRC1 nucleic acid sequence, encoding a NRC1 protein (or variant or fragment), can also be used to transform microorganisms, such as bacteria (e.g. *Escherichia coli, Pseudomonas, Agrobacterium, Bacillus,* etc.), fungi, or algae or insects, or to make recombinant viruses. Transformation of bacteria, with all or part of a NRC1 nucleic acid sequence of this invention, incorporated in a suitable cloning vehicle, can be carried out in a conventional manner, preferably using conventional electroporation techniques as described in Maillon et al. (1989, *FEMS Microbiol. Letters* 60, 205-210.) and WO 90/06999. For expression in prokaryotic host cell, the codon usage of the nucleic acid sequence may be optimized accordingly (as described for plants above). Intron sequences should be removed and other adaptations for optimal expression may be made as known.

The DNA sequence of the NRC1 nucleic acid sequence can be further changed in a translationally neutral manner, to modify possibly inhibiting DNA sequences present in the gene part and/or by introducing changes to the codon usage, e.g., adapting the codon usage to that most preferred by plants, preferably the specific relevant plant genus, as described above.

In accordance with one embodiment of this invention, the NRC1 proteins (or chimeric proteins) are targeted to intracellular organelles such as plastids, preferably chloroplasts, mitochondria, or are secreted from the cell, potentially optimizing protein stability and/or expression. Similarly, the protein may be targeted to vacuoles. For this purpose, in one embodiment of this invention, the chimeric genes of the invention comprise a coding region encoding a signal or target peptide, linked to the NRC1 protein coding region of the invention. Particularly preferred peptides to be included in the proteins of this invention are the transit peptides for chloroplast or other plastid targeting, especially duplicated transit peptide regions from plant genes whose gene product is targeted to the plastids, the optimized transit peptide of Capellades et al. (U.S. Pat. No. 5,635,618), the transit peptide of ferredoxin-NADP+oxidoreductase from spinach (Oelmuller et al., 1993, *Mol. Gen. Genet.* 237, 261-272), the transit peptide described in Wong et al. (1992, *Plant Molec. Biol.* 20, 81-93) and the targeting peptides in published PCT patent application WO 00/26371. Also preferred are peptides signalling secretion of a protein linked to such peptide outside the cell, such as the secretion signal of the potato proteinase inhibitor II (Keil et al., 1986, *Nucl. Acids Res.* 14, 5641-5650), the secretion signal of the alpha-amylase 3 gene of rice (Sutliff et al., 1991, *Plant Molec. Biol.* 16, 579-591) and the secretion signal of tobacco PR1 protein (Comelissen et al., 1986, *EMBO J.* 5, 37-40). Particularly useful signal peptides in accordance with the invention include the chloroplast transit peptide (e.g. Van Den Broeck et al., 1985, *Nature* 313, 358), or the optimized chloroplast transit peptide of U.S. Pat. No. 5,510,471 and U.S. Pat. No. 5,635,618 causing transport of the protein to the chloroplasts, a secretory signal peptide or a peptide targeting the protein to other plastids, mitochondria, the ER, or another organelle. Signal sequences for targeting to intracellular organelles or for secretion outside the plant cell or to the cell wall are found in naturally targeted or secreted proteins, preferably those described by Klösgen et al. (1989, *Mol. Gen. Genet.* 217, 155-161), Klösgen and Weil (1991, *Mol. Gen. Genet.* 225, 297-304), Neuhaus & Rogers (1998, *Plant Mol. Biol.* 38, 127-144), Bih et al. (1999, *J. Biol. Chem.* 274, 22884-22894), Morris et al. (1999, *Biochem. Biophys. Res. Commun.* 255, 328-333), Hesse et al. (1989, *EMBO J.* 8, 2453-2461), Tavladoraki et al. (1998, *FEBS Lett.* 426, 62-66.), Terashima et al. (1999, *Appl. Microbiol. Biotechnol.* 52, 516-523), Park et al. (1997, *J. Biol. Chem.* 272, 6876-6881), Shcherban et al. (1995, *Proc. Natl. Acad. Sci USA* 92, 9245-9249).

To allow secretion of the NRC1 proteins to the outside of the transformed host cell, an appropriate secretion signal peptide may be fused to the amino terminal end (N-terminal end) of the NRC1 protein. Putative signal peptides can be detected using computer based analysis, using programs such as the program Signal Peptide search (SignalP V1.1 or 2.0) (Von Heijne, Gunnar, 1986 and Nielsen et al., 1996).

In one embodiment, several NRC1 encoding nucleic acid sequences are co-expressed in a single host, optionally under control of different promoters. A co-expressing host plant is easily obtained by transforming a plant already expressing NRC1 protein of this invention, or by crossing plants transformed with different NRC1 proteins of this invention. Alternatively, several NRC1 protein encoding nucleic acid sequences can be present on a single transformation vector or be co-transformed at the same time using separate vectors and selecting transformants comprising both chimeric genes. Similarly, one or more NRC1 encoding genes may be expressed in a single plant together with other chimeric genes, for example encoding other proteins which enhance disease resistance or which are involved in the disease resistance signalling pathway, or others.

It is understood that the different proteins can be expressed in the same plant, or each can be expressed in a single plant and then combined in the same plant by crossing the single plants with one another. For example, in hybrid seed production, each parent plant can express a single protein. Upon crossing the parent plants to produce hybrids, both proteins are combined in the hybrid plant.

Preferably, for selection purposes but also for weed control options, the transgenic plants of the invention are also transformed with a DNA encoding a protein conferring resistance to herbicide, such as a broad-spectrum herbicide, for example herbicides based on glufosinate ammonium as active ingredient (e.g. Liberty® or BASTA; resistance is conferred by the PAT or bar gene; see EP 0 242 236 and EP 0 242 246) or glyphosate (e.g. RoundUp®; resistance is conferred by EPSPS genes, see e.g. EP 0 508 909 and EP 0 507 698). Using herbicide resistance genes (or other genes conferring a desired phenotype) as selectable marker further has the advantage that the introduction of antibiotic resistance genes can be avoided.

Alternatively, other selectable marker genes may be used, such as antibiotic resistance genes. As it is generally not accepted to retain antibiotic resistance genes in the transformed host plants, these genes can be removed again following selection of the transformants. Different technologies exist for removal of transgenes. One method to achieve removal is by flanking the chimeric gene with lox sites and, following selection, crossing the transformed plant with a CRE recombinase-expressing plant (see e.g. EP506763B1). Site specific recombination results in excision of the marker gene. Another site specific recombination systems is the FLP/FRT system described in EP686191 and U.S. Pat. No. 5,527,695. Site specific recombination systems such as CRE/LOX and FLP/FRT may also be used for gene stacking purposes. Further, one-component excision systems have been described, see e.g. WO9737012 or WO9500555).

Transformed Plant Cells/Plants/Seeds and Uses of the Nucleic Acid Sequence and Proteins According to the Invention In the following part the use of the NRC1 sequences according to the invention to generate transgenic plant cells, plants, plant seeds, etc. and any derivatives/progeny thereof, with an enhanced diseases resistance phenotype is described.

A transgenic plant with enhanced disease resistance can be generated by transforming a plant host cell with a nucleic acid sequence encoding at least one NRC1 protein under the control of a suitable promoter, as described above, and regenerating a transgenic plant from said cell.

Preferred promoters are promoters which are inducible by external biotic and/or abiotic stimuli. Especially promoters which are pathogen inducible are preferred, as described above. Preferred promoter—NRC1 combinations are:

a) a pathogen inducible promoter—nucleic acid sequence encoding a constitutively active NRC1 protein;
b) a pathogen inducible promoter—nucleic acid sequence encoding a wild type NRC1 protein;
c) the promoter of a plant NRC1 gene (preferably of the same species which is to be transformed)—nucleic acid sequence encoding a constitutively active NRC1 protein;
d) the promoter of a plant NRC1 gene (preferably of the same species which is to be transformed)—nucleic acid sequence encoding a wild type NRC1 protein;
e) a biotic stress inducible promoter (e.g. insect wounding inducible, pathogen inducible, etc.)—nucleic acid sequence encoding a constitutively active NRC1 protein;
f) a biotic stress inducible promoter (e.g. insect inducible, pathogen inducible, etc.)—nucleic acid sequence encoding a wild type NRC1 protein;
g) A constitutive promoter (e.g. 35S promoter)—nucleic acid sequence encoding a wild type NRC1 protein;
h) A constitutive promoter (e.g. 35S promoter)—nucleic acid sequence encoding an amino-acid sequence comprising at least 70% amino acid sequence identity to SEQ ID NO:2 over the entire length.
i) A pathogen-inducible promoter—nucleic acid sequence encoding an amino-acid sequence comprising at least 70% amino acid sequence identity to SEQ ID NO:2 over the entire length.
j) The promoter of a plant NRC1 gene—nucleic acid sequence encoding an amino-acid sequence comprising at lest 70% amino acid sequence identity to SEQ ID NO:2 over the entire length.

In one embodiment the transgenic plant may show either constitutive HR lesions or inducible HR lesions, and enhanced disease resistance to one or more pathogens. However, it is also envisaged herein that no HR lesions or "weak" HR lesions (such as smaller lesions, e.g. microlesions, and/or a low lesion frequency) develop, while the plant still shows enhanced disease resistance. NRC1 alleles or orthologs which, upon expression in host plants under control of the identical promoters, result in fewer and/or smaller HR lesions than SEQ ID NO: 1 or 3, or than the expression of the wild type NRC1 allele obtained from the same host species which is transformed, are particularly preferred herein, especially in approaches g) and h) above. Such alleles/orthologs can be referred to as NRC1 alleles conferring a "weak HR phenotype" in a given host. Such NRC1 alleles or orthologs can be identified and/or isolated as described herein above. The HR phenotype of different NRC1 alleles and/or orthologs can be compared by making expression vectors using these (preferably all nucleic acids which are to be compared are operably linked to the identical promoters, e.g. 35S), transforming plants or plant tissue with these, and by comparing the HR lesion phenotype between these plants. For Solanaceae transformants, the HR lesion phenotype of transformants expressing SEQ ID NO: 1 or 3 is preferably used as reference and any allele resulting in fewer and/or smaller HR lesions upon expression under control of the same promoter is an allele conferring a weak HR phenotype. The HR lesion phenotype can be compared and optionally quantified using various methods, such as microscopy (optionally staining dead cells), visual scoring, counting lesions to calculate the number per cm², measuring the diameter of HR lesions, etc.

Preferably, the transgenic plants of the invention comprise enhanced disease resistance against one or more pathogens, especially biotrophic and/or hemibiotrophic pathogens of the transgenic plant species. Thus, for example transgenic tomato or potato plants comprise enhanced resistance to at least one, or more, of the fungal, bacterial, nematode species and/or viral pathogens listed above, most preferably at least against one or several biotrophic and/or hemibiotrophic species.

"Disease resistance" or "increased/enhanced disease resistance" is used herein to refer to an enhanced ability of transformants (compared to wild type or control transformants) to withstand the attack of one or more plant pathogens, or in other words, it refers to a significant reduction in disease symptoms in transformants compared to non-transformed (or empty-vector transformed) controls. Disease resistance or enhanced disease resistance may be determined using a variety of methods. Often disease symptoms are scored visually (either in bioassays or in the field) by assessing the disease symptoms at one or more time points after inoculation or contact with a pathogen. Alternative methods include methods whereby the pathogen is detected and optionally quantified. A transgenic plant may thus show enhanced disease resistance if the amount of pathogen detected in/on the tissue is significantly less compared to controls, or if the pathogen spread is significantly slower than in controls. Ultimately, a significant increase in average yield of transformants (e.g. at least 1%, 2%, 5%, 10% or more) compared to controls, when grown under equivalent disease pressure (preferably in the field) provides an indirect measurement of enhanced disease resistance.

Thus, a plurality of transformed plants expressing NRC1 protein (or a constitutively active NRC1 protein) show enhanced disease resistance if they show a significant reduction of disease symptoms, compared to the untransformed or empty-vector transformed controls. Obviously, statistical analysis is required to determine whether significant difference exist. Preferably, one or more disease symptoms are on average at least 2%, 5%, 10%, 15%, 20%, 30%, 40%, 50%, or even 100% lower in NRC1 transformants than in the control plants. As the disease assay is different for every host-pathogen combination, no specific protocol can be provided, but the skilled person knows how to determine whether transformants show significantly enhanced disease resistance to one or more pathogens. Bioassays as known in the art for each plant-pathogen combination can be used to compare resistance of transgenic plants to suitable controls.

As the NRC1 protein may in some embodiments result in HR lesions in the absence of pathogen (for example if the NRC1 gene is under the control of a constitutive promoter): it may in certain embodiments be important to differentiate between symptoms caused by NRC1 expression and symptoms caused by pathogen infection and spread. It may, therefore, be preferred to use methods which detect the pathogen itself (rather than necrosis on the plant tissue) and to compare the amount of pathogen present or the speed of pathogen spread. For example, bioassays may be used wherein the pathogen can be detected by staining. In the examples a transgenic *C. fulvum* race is used which expresses GUS. Fungal mycelium can, therefore, be visualized using X-gluc staining of the inoculated plant tissue. A significant reduction of fungal mycelium in the transgenic plants compared to the controls indicates an enhanced resistance to the fungus.

It is also an embodiment to generate transgenic plants which express several NRC1 proteins, preferably under the control of different promoters, such as different pathogen inducible promoters.

The disease resistance phenotype can be fine-tuned by expressing a suitable amount of NRC1 protein at a suitable time and location. Such fine-tuning may be done by determining the most appropriate promoter for a particular host-pathogen combination and also by selecting transgenic "events" which show the desired expression level. A too low level of NRC1 protein or too slow induction of NRC1 protein production following pathogen attack may be insufficient to enhance disease resistance levels. On the other hand, a too high protein level or expression at times and locations devoid of pathogen attack, may result in agronomically undesired phenotypes, such as lesions in leaves or fruit in the absence of pathogens and yield penalties. However, the skilled person can easily generate plants having enhanced disease resistance, but which at the same time are agronomical acceptable. Optimal NRC1 alleles may be isolated or identified as described, e.g. alleles providing high resistance levels and only a weak HR phenotype.

Transformants expressing desired levels of the NRC1 protein are selected by e.g. analysing copy number (Southern blot analysis), mRNA transcript levels (e.g. RT-PCR using NRC1 primer pairs or flanking primers) or by analysing the presence and level of NRC1 protein in various tissues (e.g. SDS-PAGE; ELISA assays, etc). For regulatory reasons, preferably single copy transformants are preferably selected and the sequences flanking the site of insertion of the chimeric gene is analysed, preferably sequenced to characterize the "event". High or moderate NRC1 expressing transgenic events are selected for further crossing/backcrossing/selfing until a high performing elite event with a stable NRC1 transgene is obtained.

Transformants expressing one or more NRC1 genes according to the invention may also comprise other transgenes, such as other genes conferring disease resistance or conferring tolerance to other biotic and/or abiotic stresses. To obtain such plants with "stacked" transgenes, other transgenes may either be introgressed into the NRC1 transformants, or the NRC1 transformants may be transformed subsequently with one or more other genes, or alternatively several chimeric genes may be used to transform a plant line or variety. For example, several chimeric genes may be present on a single vector, or may be present on different vectors which are co-transformed.

In one embodiment the following genes are combined with one or more NRC1 genes according to the invention: known disease resistance genes, especially genes conferring enhanced resistance to necrotophic pathogens, virus resistance genes, insect resistance genes, abiotic stress resistance genes (e.g. drought tolerance, salt tolerance, heat- or cold tolerance, etc.), herbicide resistance genes, and the like. The stacked transformants may thus have an even broader biotic and/or abiotic stress tolerance, to pathogen resistance, insect resistance, nematode resistance, salinity, cold stress, heat stress, water stress, etc. Also, NRC1 silencing approaches may be combined with NRC1 expression approaches in a single plant. For example, NRC1 overexpression in roots or tubers may confer or enhance root or tuber resistance to soil pathogens. At the same time downregulation of NRC1 in aerial parts may confer or enhance resistance to necrotrophic pathogens (or vice versa).

It is also possible to introduce or introgress the NRC1 gene into a plant breeding line which already has a certain level of disease resistance. For durability of disease resistance in the field, it may be desirable to stack several disease resistance mechanisms in a plant, preferably whereby the resistance sources have different underlying molecular mechanisms.

Whole plants, seeds, cells, tissues and progeny (such as F1 hybrids, F2 seeds/plants, etc.) of any of the transformed plants described above are encompassed herein and can be identified by the presence of the transgene in the DNA, for example by PCR analysis using total genomic DNA as template and using NRC1 specific PCR primer pairs. Also "event specific" PCR diagnostic methods can be developed, where the PCR primers are based on the plant DNA flanking the inserted chimeric gene, see U.S. Pat. No. 6,563,026. Similarly, event specific AFLP fingerprints or RFLP fingerprints may be developed which identify the transgenic plant or any plant, seed, tissue or cells derived there from.

It is understood that the transgenic plants according to the invention preferably do not show non-desired phenotypes, such as yield reduction, enhanced susceptibility to diseases (especially to necrotrophs) or undesired architectural changes (dwarfing, deformations) etc. and that, if such phenotypes are seen in the primary transformants, these can be removed by normal breeding and selection methods (crossing/backcrossing/selfing, etc.). Any of the transgenic plants described herein may be homozygous or hemizygous for the transgene.

NRC1 Gene Silencing Approaches and Gene Silencing Vectors

It is a further embodiment of the invention to provide plants with enhanced disease resistance, especially against necrotrophic pathogens, whereby the plant is transformed with an NRC1 gene silencing vector. Without limiting the scope of the invention, it is thought that silencing of endogenous NRC1 genes or gene families results in the inability of the transgenic plant to trigger and/or mount an HR response. As necrotrophic pathogens require cell death for their growth and development, such plants may comprise enhanced resistance to one or more necrotrophic pathogens.

"Gene silencing" refers to the down-regulation or complete inhibition of gene expression of one or more target genes (e.g. endogenous NRC1 genes). The use of inhibitory RNA to reduce or abolish gene expression is well established in the art and is the subject of several reviews (e.g. Baulcombe 1996, Stam et al. 1997, Depicker and Van Montagu, 1997). There are a number of technologies available to achieve gene silencing in plants, such as chimeric genes which produce antisense RNA of all or part of the target gene (see e.g. EP 0140308 B1, EP 0240208 B1 and EP 0223399 B1), or which produce sense RNA (also referred to as co-suppression), see EP 0465572 B1.

The most successful approach so far has however been the production of both sense and antisense RNA of the target gene ("inverted repeats"), which forms double stranded RNA (dsRNA) in the cell and silences the target gene. Methods and vectors for dsRNA production and gene silencing have been described in EP 1068311, EP 983370 A1, EP 1042462 A1, EP 1071762 A1 and EP 1080208 A1. A vector according to the invention may, therefore, comprise a transcription regulatory region which is active in plant cells operably linked to a sense and/or antisense DNA fragment of a NRC1 gene according to the invention. Generally short (sense and antisense) stretches of the target gene sequence, such as 17, 18, 19, 20, 21, 22 or 23 nucleotides of coding or non-coding sequence are sufficient. Longer sequences can also be used, such as 50, 100, 200 or 250 nucleotides or more. Preferably, the short sense and antisense fragments are separated by a spacer sequence, such as an intron, which forms a loop (or hairpin) upon dsRNA formation. Any short stretch of SEQ ID NO: 1 or 3, or variants thereof, may be used to make a NRC1 gene silencing vector and a transgenic plant in which one or more NRC1 genes are silenced in all or some tissues or organs (depending on the promoters used). A convenient way of generating hairpin constructs is to use generic vectors such as pHANNIBAL and pHELLS-GATE, vectors based on the Gateway® technology (see Wesley et al. 2004, *Methods Mol Biol.* 265:117-30; Wesley et al. 2003, *Methods Mol Biol.* 236:273-86 and Helliwell & Waterhouse 2003, *Methods* 30(4):289-95.), all incorporated herein by reference.

By choosing conserved nucleic acid parts of the NRC1 gene, NRC1 family members in a host plant or plant parts can be silenced. Encompassed herein are also transgenic plants comprising a transcription regulatory element operably linked to a sense and/or antisense DNA fragment of a NRC1 gene and exhibiting enhanced resistance to one or more pathogens, especially necrotrophic pathogens.

Also, plants having enhanced resistance to one or more biotrophic and/or hemi-biotrophic pathogens and to one or more necrotrophic pathogens are provided. Such plants can be generated by choosing appropriate promoter—NRC1 gene combinations. For example a functional NRC1 protein may be produced in a certain tissue at a certain time (e.g. upon induction or in aerial plant parts), providing resistance to biotrophic and/or hemibiotrophic pathogens, while the endogenous NRC1 gene(s) are silenced in a different tissue and/or at a different time (e.g. in seedlings, in roots or tubers, etc.), thereby providing resistance to one or more necrotrophic pathogens. A single plant may, therefore, comprise both a chimeric NRC1 expressing transgene and an NRC1 silencing gene.

Mutant Alleles and Plants According to the Invention

It is also an embodiment of the invention to use non-transgenic methods, e.g. mutagenesis systems such as TILL-ING (Targeting Induced Local Lesions IN Genomics; McCallum et al., 2000, *Nat Biotech* 18:455, and McCallum et al. 2000, *Plant Physiol.* 123, 439-442, both incorporated herein by reference) and selection to generate plant lines which produce higher levels of one or more NRC1 proteins according to the invention and/or which produce a constitutively active NRC1 protein as described. Without limiting the scope of the invention, it is believed that such plants could comprise point/deletion mutations in the promoter that are binding sites for repressor proteins that would make the host NRC1 gene constitutive or higher in expression. Constitutively active NRC1 mutants will comprise mutations in the coding region, such as the MHD region. Preferably NRC1 protein levels in the mutant or parts of the mutant are at least about 2, 5, 10, 15%, or more, increased in the mutant compared to non-mutant plants. TILLING uses traditional chemical mutagenesis (e.g. EMS mutagenesis) followed by high-throughput screening for mutations (e.g. using Cel 1 cleavage of mutant-wild type DNA heteroduplexes and detection using a sequencing gel system), see e.g. Henikoff et al. *Plant Physiology Preview* May 21, 2004. Thus, non-transgenic plants, seeds and tissues comprising an enhanced NRC1 gene expression in one or more tissues and comprising one or more of the NRC1 phenotypes according to the invention (enhanced disease resistance and/or HR lesions) and methods for generating and identifying such plants is encompassed herein.

The method comprises in one embodiment the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants. Seeds may for example be radiated or chemically treated and the plants screened for a modified phenotype, such as enhanced disease resistance and/or HR lesions.

In another embodiment of the invention, the plant materials are natural populations of the species or related species that comprise polymorphisms or variations in DNA sequence at the NRC1 orthologous coding and/or regulatory sequence. Mutations at the NRC1 gene target can be screened for using a ECOTILLING approach (Henikoff et al 2004, supra). In this method natural polymorphisms in breeding lines or related species are screened for by the above described TILLING methodology, in which individual or pools of plants are used for PCR amplification of the NRC1 target, heteroduplex formation and high-throughput analysis. This can be followed up by selecting of individual plants having the required mutation that can be used subsequently in a breeding program to incorporate the desired NRC1-orthologous allele to develop the cultivar with desired trait.

Mutant plants can be distinguished from non-mutants by molecular methods, such as the mutation(s) present in the DNA, NRC1 protein levels, NRC1 RNA levels etc, and by the modified phenotypic characteristics.

The non-transgenic mutants may be homozygous or heterozygous for the mutation.

Sequences Referred to

SEQ ID NO 1: coding region of the tomato NRC1 gene

SEQ ID NO 2: amino acid sequence of the tomato NRC1 protein

SEQ ID NO 3: full length cDNA of the tomato NRC1 gene (including 5' and 3' UTR)

SEQ ID NO 4: amino acid sequence of the tomato NRC1$^{D481V}$ protein

SEQ ID NO 5: 3'UTR of the tomato NRC1 gene

The following non-limiting Examples illustrate the different embodiments of the invention. Unless stated otherwise in the Examples, all recombinant DNA techniques are carried out according to standard protocols as described in Sambrook et al. (1989) *Molecular Cloning: A Laboratory Manual,* Second Edition, Cold Spring Harbor Laboratory Press, and Sambrook and Russell (2001) *Molecular Cloning: A Laboratory Manual,* Third Edition, Cold Spring Harbor Laboratory Press, NY; and in Volumes 1 and 2 of Ausubel et al. (1994) *Current Protocols in Molecular Biology, Current Protocols,* USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

EXAMPLES

1. Material and Methods 1.1 VIGS in *N. benthamiana,* Agroinfiltration, HR and Disease Assays Four-week-old *N. benthamiana* plants were agroinfiltrated with a 1:1 mixture of pTV00-derived constructs (binary TRV RNA2 vector) and pBintra6 (binary TRV RNA1 vector) (Ratcliff et al., 2001 *Plant J.* 25, 237-245), or a 1:1 mixture of pTRV-RNA2-derived constructs and pTRV-RNA1 (Liu et al., 2002, *Plant J.* 31, 777-786; Liu et al., 2002, *Plant J.* 30, 415-429). The following TRV constructs were used: TRV:NRC1, TRV:Cf-4 and TRV:SGT1 (Peart et al., 2002, *Proc. Natl. Acad. Sci.* USA 99, 10865-10869), all in the TRV vector described by Ratcliff et al. (2001, supra) and TRV:EDS1, TRV:MEK2, TRV:RAR1 and TRV:NDR1 (Ekengren et al., 2003, *Plant J.* 36, 905-917), all in the TRV vector described by Liu et al. (2002, *Plant J.* 30, 415-429). For each TRV construct, in each experiment four plants were used. AvrPto and CP were agroinfiltrated in TRV-infected *N. benthamiana* expressing the resistance gene Pto (*N. benthamiana*:Pto (line 38-12 (Rommens et al., 1995, *Plant Cell* 7, 1537-1544)) (Pedley and Martin, 2003, *Annu. Rev. Phytopathol.* 41, 215-243) and Rx (*N. benthamiana*:Rx (line Rx-18) (Bendahtnane et al., 1999, *Plant Cell* 11, 781-791), respectively. In all other cases Agroinfiltration was performed in *N. benthamiana* expressing the resistance gene Cf-4 (*N. benthamiana*:Cf-4). Three weeks post TRV inoculation the third, fourth and fifth leaf above the inoculated leaves were challenged with *Agrobacterium tumefaciens* that directs expression of AvrPto ($OD_{600}$=0.06) (Tang et al., 1996, *Science* 274, 2060-2063), CP ($OD_{600}$=0.12) (Bendahmane et al., 1999, supra), Avr4 ($OD_{600}$=0.03), Cf-9 and Avr9 (mixed in a 1:1 ratio, $OD_{600}$=0.2) (Van der Hoorn et al., 2000 *Mol. Plant-Microbe Interact.* 13, 439-446), LeEix2 and tvEix (mixed in a 1:1 ratio, $OD_{600}$=1) (Ron and Avni, 2004, *Plant Cell* 16, 1604-1615), the β-glucuronidase (GUS) gene ($OD_{600}$=2) (Van der Hoorn et al., 2000, *Mol. Plant-Microbe Interact.* 13, 439-446), NRC1 and p19 (mixed in a 1:1 ratio, $OD_{600}$=1) (Voinnet et al., 2003, *Plant J.* 33, 949-956), the constitutively active NRC1$^{481V}$ or the inactive NRC1$^{K191R/D481V}$ double mutant ($OD_{600}$=2), LeMAPKKKα$^{KD}$, LeMAPKKKα$^{KD-}$ (Del Pozo et al., 2004, *EMBO J.* 23, 3072-3082) (both at $OD_{600}$=0.12) or LeMEK2DD and LeMEK2 (Del Pozo et al., 2004, supra) (both at $OD_{600}$=0.25). Two days post infiltration of LeMAPKKKα$^{KD}$, LeMAPKKKα$^{KD-}$, LeMEK2DD or LeMEK2 the leaves were sprayed with a 7.5 µM solution of 17-β-estradiol in water, containing silwet (4 µl/100 ml) (Del Pozo et al., 2004, supra). For protein injections, Avr4-HIS-FLAG-tagged protein was treated with enterokinase EK-max according to the manufacturer's recommendations (Invitrogen, Breda, NL) and 5 µM Avr4 protein in water, supplemented with 0.2% tween (v/v) was used for injections. Three to five days post agroinfiltration or protein injection the leaves were examined for the development of an HR, or assayed for β-glucuronidase (GUS) activity.

1.2 VIGS in Tomato, HR and Disease Assays

For VIGS in tomato the pTRV-RNA1 and pTRV-RNA2 vectors described by Liu et al. (2002, *Plant J.* 30, 415-429) were used. The Cf-4 and NRC1 fragments were excised from pTV00 by digestion with BamH1/Asp718 and inserted into BamH1/Asp718-digested pTRV-RNA2 (pYL156) (Liu et al., 2002, *Plant J.* 31, 777-786). To construct TRV:222-UTR, part of the 3'-UTR of NRC1 was amplified using primers 222-3'UTR-F (5'-GT GGATCCGCAGGTTCAACCAGCCTGGT-3'; BamH1 site underlined) and 222-3'UTR-R (5'-GT GGTACCCAAGTGACTTGTTCTGCTGT-3'; Asp718 site underlined) and to construct TRV:222-LRR, part of the NRC1 region coding the LRRs was amplified using primers 222-LRR-F (5'-GT GGATCCGTTAAGAGGCTGCAATTTCT-3'; BamH1 site underlined) and 222-LRR-R (5'-GT GGTACCGATCTTCTCAAGTTTATCAC-3'; Asp718 site underlined). The PCR fragments were BamH1/Asp718-digested and inserted into BamH1/Asp718-digested pTRV-RNA2. TRV:Prf construction has been described (Ekengren et al., 2003, *Plant J.* 36, 905-917). All plasmids were transformed to *A. tumefaciens* strain GV3101 by electroporation (Takken et al., 2000, *Plant J.* 24, 275-283). To establish VIGS in tomato, cotyledons of ten- to twelve-day-old tomato seedlings were agroinfiltrated with a mixture of pTRV-RNA1 and the pTRV-RNA2-derived constructs (combined in a 1:1 ratio) (Liu et al., 2002, supra). For each TRV construct either four Cf-4-containing tomato plants (Cf0 plants transformed with Hcr9-4D (Cf-4)) (Thomas et al., 1997, *Plant Cell* 9, 2209-2224), resistant to *C. fulvum* expressing Avr4, or four Cf-9-containing tomato plants (Cf0 plants transformed with Hcr9-9C (Cf-9)) (Jones et al., 1994, *Science* 266, 789-793), resistant to *C. fulvum* expressing Avr9, were used. As control Cf0 tomato plants (MM-Cf0), fully susceptible to *C. fulvum*, either TRV:00- or TRV:NRC1-inoculated were used. For disease assays, three weeks post TRV inoculation Cf0 and Cf-4-containing plants were inoculated with *C. fulvum* (De Wit, 1977, *Neth. J. Plant Path.* 83, 109-122). A *C. fulvum* race 5-pGPD::GUS was used (expressing Avr4 and the β-glucuronidase gene under control of the constitutive GPD promoter). Colonization of the leaflets was assessed two weeks later by X-gluc staining. In parallel, leaflets of the second, third or fourth compound leaf of the plants were used for RT-PCR analysis to test for 'knock down' of the gene of interest (see below). For HR assays, leaflets of the third compound leaf of TRV-infected Cf-4- or Cf-9-containing plants were injected with Avr4 or Avr9, respectively. Both elicitors were injected into leaflets with a micro-syringe (Ito Corporation, Fuji, Japan). Avr4 was injected at a concentration of 10 μM. at ten sites per leaflet and four leaflets per plant. For Avr9, eight times diluted apoplastic fluid containing about 10 μM of Avr9, isolated from a compatible interaction between race 5 of *C. fulvum* and Cf0 plants, was injected at eight sites per leaflet and four leaflets per plant. Resistance against *Pseudomonas syringae* pv. tomato was assayed in tomato RG-PtoR (Pto/Pto, Prf/Prj), inoculated with TRV:00, TRV:Prf or TRV:NRC1. The inoculation procedure and the determination of bacterial colonization of the leaves were performed as described previously (Ekengren et al., 2003, supra).

1.3 Binary 35S:NRC1 Vector Construction and Mutagenesis

Full length NRC1 cDNA was PCR-amplified using primers 222-Start-F (5'-GGGAT CCATGGTTGATGTAGGGGTTGA-3') and 222-Stop-R (5'-GTCACTGCAGACCTTTCTAAGAAGCTGTCTG-3'), thereby introducing NcoI and PstI restriction sites, respectively (restriction sites underlined). The PCR fragment was NcoI/PstI-digested and inserted into NcoI/PstI-digested pRH80 (Van der Hoorn et al., 2000, *Mol. Plant-Microbe Interact.* 13, 439-446). Subsequently, the construct was XbaI/KpnI-digested and the resulting fragment containing the 35S promoter, the NRC1 open reading frame and the NOS terminator (tNOS), was cloned into the XbaI/KpnI-digested pMOG800 binary vector (Honée et al., 1998, *Plant Physiol.* 117, 809-820) to create plasmid NRC1(wt). To create constitutively active binary NRC1$^{D481V}$, the D481V mutation was introduced by overlap extension PCR (Higuchi et al., 1988, *Nucleic Acids Res.* 16, 7351-7367) using the NRC1wt plasmid as a template and flanking primers 222-Start-F and 222-Stop-R and mismatch primers 222MHD-F (5'-CAAAACTTGTCGTGTTCATG TCATGTTGTATGAG-3') and 222MHD-R (5'-CCAG-CAAAACTCATACAACATGACATGAACACGAC-3') (mutation underlined).

The fragment was NcoI/PstI-digested, inserted into pRH80 and the 35S-NRC1$^{D481V}$-tNOS fragment was excised and subsequently inserted into pMOG800 as described above. In a similar way the P-loop mutant NRC1$^{K191R}$, and the inactive double mutant NRC1$^{K191R/D481V}$ were created. Here, the K191R mutation was introduced using mismatch primers 222Ploop-F (5'-GGAATGCCTG-GTCTTGGCAGAACTACACTAGC-3') and 222Ploop-R (5'-GCTAGTGTAGTT CTGCCAAGACCAGGCATTCC-3') (mutation underlined) with respectively plasmid NRC1(wt) and NRC1$^{D481V}$ as a template. All constructs were sequence-verified and transformed to *A. tumefaciens* strain GV3101.

1.4 DNA Gel-Blot Analysis

Genomic DNA from *N. benthamiana* was isolated using the QIA-Gen DNA extraction protocol (Qiagen, Venlo, NL), whereas for tomato the standard protocol described by (Sambrook and Russell, 2001, Molecular cloning: A Laboratory Manual, 3rd ed. (Cold Spring Harbor, N.Y., U.S.A.: Cold Spring Harbor Laboratory Press) was used. The DNA was digested with BamHI, HindIII, EcoRI, EcoRV or XbaI. The *N. benthamiana* gel-blot was hybridized with the $^{32}$P-labeled (Prime-a-gene Labeling System, Promega, Madison, Wis.) 252 bp fragment present in the TRV:NRC1 vector and the DNA gel-blot of tomato was hybridized with a $^{32}$P-labeled probe of 1293 bases corresponding to nucleotides 1876 to 3168 of the full length NRC1 cDNA. Sites for the restriction enzymes used are not present in the probes. Low stringency refers to washing at 55° C. in 2×SSC and 0.5% SDS. High stringency conditions consist of washing at 65° C. in 0.5×SSC and 0.5% SDS.

1.5 RT-PCRs to Show Silencing of NRC1 in Tomato

Four leaf discs (approximately 100 mg of tissue in total) were collected from the second, third or fourth compound leaf of TRV-infected plants. Total RNA was extracted using the QIA-Gen RNAeasy extraction protocol (Qiagen, Venlo, NL) and treated with RNase-Free DNase (Bio-Rad, Veenendaal, NL). First strand cDNA was synthesized from 1 μg of total RNA using the Bio-Rad cDNA synthesis kit (Bio-Rad, Veenendaal, NL) and RT-PCR was performed using the following cycles: 95° C. for 15 sec, 60° C. for 45 sec and 72° C. for 60 sec. The primers that were used (222F: 5'-TGAGGTATATTGCTTTCTCATCTGAC-3' and 222R: 5'-AGCTATTTTCCCACGGATGCCCAG-3') do not cover the fragment which is inserted in TRV:NRC1. Actin primers (ActinFnr182: 5'-TATGGAAACATTGTGCTCAGTGG-3' and ActinRnr183: 5'-CCAGATTCGTCATACTCTGCC-3') were used to check for the presence of equal amounts of cDNA in the PCR reactions.

Example 2

Results 2.1 Tomato NRC1; a CC-NB-LRR Protein cDNA-AFLP analysis was performed, followed by VIGS of the identified fragments of tomato in *N. benthamiana*:Cf-4. 20 cDNA fragments were identified of which VIGS affects the Cf-4/Avr4-induced HR. For one of these, NRC1, the full length cDNA was isolated, as depicted in SEQ ID NO: 3. The open reading frame is shown in SEQ ID NO: 1, which encodes the NRC1 protein depicted in SEQ ID NO: 2.

The predicted primary structure of the NRC1 protein (SEQ ID NO: 2) typically resembles that of CC-NB-LRR resistance proteins (FIG. 1). NRC1 has an amino-terminal coiled-coil (CC) domain, an NB-ARC (Nucleotide Binding adapter shared by Apaf-1, R proteins and CED4) domain (Van der Biezen and Jones, 1998, *Curr. Biol.* 8, R226-R227; Aravind et al., 1999, *Trends Biochem. Sci.* 24, 47-53) and 13 imperfect leucine-rich repeats (LRRs). As indicated in FIG. 1, comparison with homologous NB-ARC domains revealed the presence of a Kinase1A or P-loop motif, four RNBS (Resistance Nucleotide Binding Site) motifs and a GLPL and MHD motif (Meyers et al., 1999, *Plant J.* 20, 317-332; Meyers et al., 2003, *Plant Cell* 15, 809-834).

The 252 bp cDNA-AFLP fragment present in the TRV:NRC1 vector used for VIGS codes for amino acids 599-681, which are located in LRRs four to seven.

Low stringency DNA gel-blot analysis of genomic DNA of tomato digested with the BamHI-, HindIII-, EcoRI-, EcoRV- and XbaI, was hybridized with a 1293 bp NRC1 cDNA fragment (nucleotides 1876 to 3168 of SEQ ID NO: 3) covering the NRC1 sequence present in the TRV:NRC1-, TRV:NRC1-LRR- and TRV:NRC1-UTR constructs (see below) as a probe. This Southern blot revealed only one prominent band after a high stringency wash, which indicates that NRC1 is a single-copy gene in tomato.

A gel blot of BamHI-, HindIII-, EcoRI-, EcoRV- and XbaI-digested genomic DNA of *N. benthamiana* was probed with the tomato NRC1 cDNA-AFLP fragment present in the TRV vector and two-three hybridizing bands were found (results not shown) (0.5×SSC, 0.5% SDS, 65° C.). This suggests that there are at least two to three NRC1 orthologs present in the genome of *N. benthamiana* that can be silenced upon inoculation with TRV:NRC1.

2.2 NRC1-Silenced Tomato is Affected in Cf-4-Mediated HR and Disease Resistance

To investigate the function of NRC1 in HR-signaling and resistance to *C. fulvum*, the inventors performed VIGS in tomato, since this plant is the only host for this fungus. Ten-day-old tomato seedlings were agroinfiltrated with TRV:NRC1 and three weeks post infiltration RNA was isolated from potentially silenced leaflets and analyzed by RT-PCR. The NRC1 transcript levels varied in different TRV:NRC1-infected plants, but in most cases they were lower than in the TRV:00-infected plants, indicating that 'knock-down' of NRC1 expression had occurred (data not shown).

To exclude the possibility that the phenotype that we observe in tomato is caused by silencing of additional NB-LRR proteins, we also performed VIGS in tomato using a 360 bp fragment of NRC1 targeted to LRRs eight to twelve (TRV:NRC1-LRR), and a fragment consisting of 297 bp of the 3'-untranslated region (UTR) of NRC1 (TRV:NRC1-UTR). With these constructs we tested whether NRC1 is required for Cf-4-mediated HR in tomato by Avr4 protein injections in TRV:222-LRR and TRV:222-UTR-infected, Cf-4-containing tomato plants. Silencing of NRC1 (using each of the three constructs) results in a mild phenotype as the tomato plants appeared somewhat smaller than the TRV:00- or TRV:Cf-4-infected plants (data not shown). As controls Avr4 protein was injected in TRV:00- and TRV:Cf-4-infected plants. In TRV:Cf-4-infected plants the percentage of responding Avr4-injected sites was 52% (FIG. 2), indicating a decreased HR due to silencing of Cf-4. In TRV:222-LRR and TRV:222-UTR-infected plants this percentage was similar (56% and 48%, respectively) (FIG. 2), confirming the function of NRC1 in Cf-4/Avr4-induced HR, also in tomato. Similar results were obtained upon VIGS of Nrc1 in Cf-9-containing tomato and subsequent injections of apoplastic fluid containing Avr9 (not shown). For VIGS of Cf-9 in Cf-9-containing tomato we used the TRV:Cf-4 construct, since the 404 bp Cf-4 fragment codes for the highly conserved LRRs 15 to 21, enabling silencing of both Cf-4 as well as the homologous Cf-9 resistance gene (Van der Hoorn et al., 2001, supra).

Further, it was investigated whether NRC1 is also required for full resistance of tomato to *C. fulvum*. Cf0 and Cf-4-plants were inoculated with TRV:00, TRV:Cf-4 and TRV:NRC1 and after three weeks silenced plants were inoculated with a strain of *C. fulvum* expressing Avr4 and the β-glucuronidase (GUS) gene, thereby allowing visualization of fungal growth. Two weeks post *C. fulvum* inoculation leaves were stained with X-gluc. In leaflets of Cf-4 plants infected with TRV:00 no growth of *C. fulvum* was detected, whereas in TRV:Cf-4-infected Cf-4 plants patches of blue staining indicate compromised Cf-4-mediated resistance (not shown). Also in TRV:NRC1-infected plants small patches of blue staining indicate loss of full resistance against the fungus. Microscopical analysis revealed intercellular growth of fungal hyphae in TRV:Cf-4- and TRV:NRC1-infected plants, but not in the TRV:00-infected control plants. All Cf0 plants displayed extensive colonization by *C. fulvum*, indicating that neither the TRV infection itself, nor VIGS using TRV:NRC1 affects the susceptibility of these plants to the fungus.

2.3 VIGS of NRC1 Affects the HR Induced by Different Matching R Gene/Avr Gene Combinations In addition to a decreased Cf-4/Avr4-induced HR upon VIGS using NRC1, it was found that also the HR induced by the Inf1 elicitor of the oomycete pathogen *Phytophthora infestans* is decreased upon VIGS using NRC1 in *N. benthamiana*. To further investigate the specificity of NRC1 in defense signaling, the inventors tested its requirement for the HR induced by additional R/Avr combinations. As controls TRV:00 (empty vector) and TRV:SGT1 were included, since SGT1 is known to be required for the HR induced by several R/Avr combinations (Peart et al., 2002, *Proc. Natl. Acad. Sci.* USA 99, 10865-10869).

Agroinfiltration of a mix of Cf-9 and Avr9 (Van der Hoorn et al., 2000, supra), or a mix of LeEix2 and tvEix (Ron and Avni, 2004, *Plant Cell* 16, 1604-1615) in TRV:NRC1-infected *N. benthamiana* resulted in a decreased HR, whereas in the TRV:00-infected plants the HR developed normally. In TRV:SGT1-infected plants the HR was completely abolished, confirming the observations of Peart et al. (2002, supra) (FIG. 3). Also AvrPto from the bacterial pathogen *Pseudomonas syringae* pv tomato and the gene encoding the coat protein (CP) of potato virus X (PVX) were agroinfiltrated in TRV-infected *N. benthamiana* expressing the resistance gene Pto (Pedley and Martin, 2003, *Annu. Rev.*

*Phytopathol.* 41, 215-243) and Rx (Bendahmane et al., 1999, *Plant Cell* 11, 781-791), respectively. In both cases plants infected with TRV:00 showed an HR, while the HR was abolished in TRV:SGT1-infected plants. TRV:NRC1-infection resulted in a severely suppressed Pto/AvrPto- as well as Rx/CP-induced HR, indicating that in *N. benthamiana* an NRC1 protein is required for HR signaling activated by several R/Avr gene-for-gene combinations (FIG. 3).

To exclude the possibility that the compromised HR in TRV:NRC1-infected *N. benthamiana* results from a decreased transformation efficiency by *Agrobacterium*, the inventors infiltrated TRV:00- and TRV:NRC1-infected *N. benthamiana*:Cf-4 with *Agrobacterium* expressing the β-glucuronidase (GUS) gene (Van der Hoorn et al., 2000, supra). Three days post infiltration a similar intensity of the blue staining in TRV:00- and TRV:NRC1-infected plants revealed that the transformation efficiency of the plants by *Agrobacterium* is not affected (data not shown). In addition, the TRV:NRC1-infected plants also showed a reduced HR upon injection with Avr4 protein, while in TRV:00-infected plants a clear HR developed within 2 days.

2.4 NRC1 Acts Downstream of EDS1 and Upstream of the MAPK Cascade in a Cell Death Signaling Pathway Since NRC1 is required not only for Cf-4/Avr4-induced HR, but also for HR induced by several additional R/Avr combinations, NRC1 appears to be involved in a common HR signaling pathway. A typical host response that precedes the initiation of the HR includes activation of MAPK cascades (Romeis et al., 2001, *EMBO J.* 20, 5556-5567; Del Pozo et al., 2004, *EMBO J.* 23, 3072-3082; Pedley and Martin, 2005, *Plant Biol.* 8, 541-547).

Figure 4A:
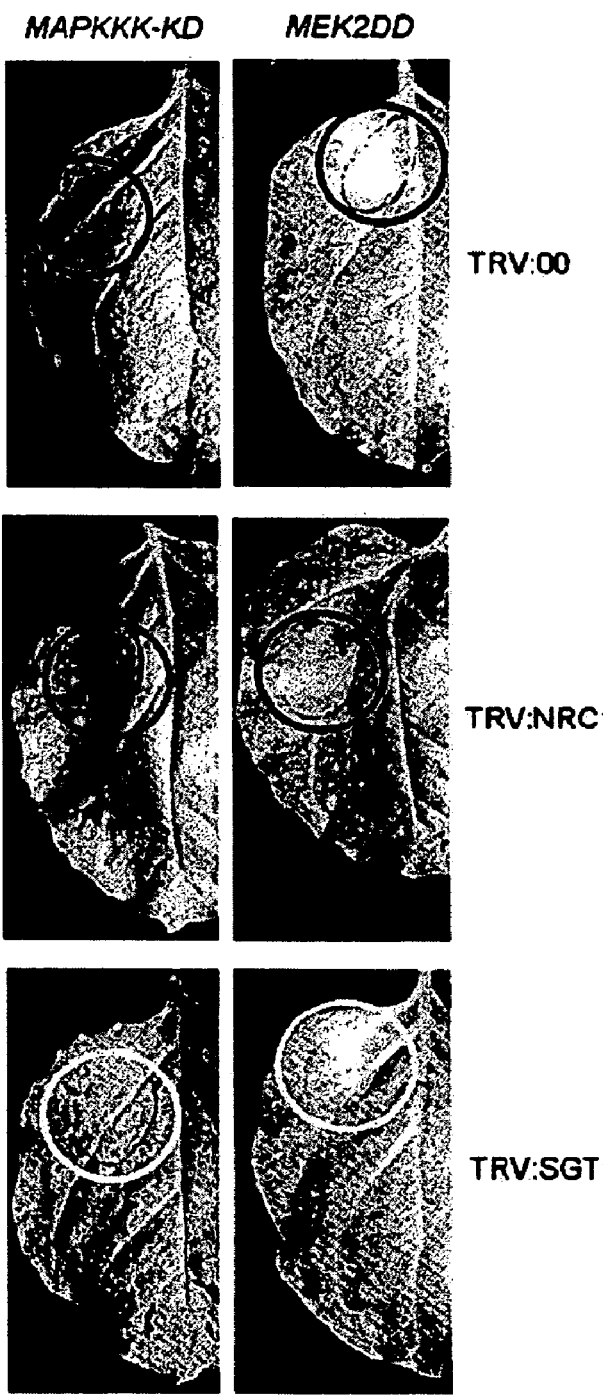

To investigate the requirement of NRC1 for the HR initiated by MAPKs, epistasis experiments in *N. benthamiana* were performed. Plants were inoculated with TRV:00, TRV:SGT1 and TRV:NRC1 and subsequently agroinfiltrated with genes encoding the kinase domain of LeMAPKKKα (LeMAPKKKα$^{KD}$) or constitutively active LeMEK2 (LeMEK2DD) (Yang et al., 2001, *Proc. Natl. Acad. Sci. USA* 98, 741-746; Del Pozo et al., 2004, *EMBO J.* 23, 3072-3082.). Two days post agroinfiltration expression of the genes was induced by spraying the infiltrated leaves with estradiol. Transient expression of each of the genes results in an HR in TRV:00-infected plants, whereas in TRV:SGT1-infected plants the HR is decreased (FIG. 4A). In TRV:NRC1-infected plants the HR caused by both constitutively active kinases is not affected (FIG. 4A). Agroinfiltration of the corresponding negative controls, LeMAPKKKα$^{KD-}$ and wild-type LeMEK2 did not result in an HR in any of the TRV-infected plants (data not shown). These results indicate that SGT1 is functional downstream of these MAPKs, whereas the MAPKs act either downstream or independent of NRC1.

Figure 4B:
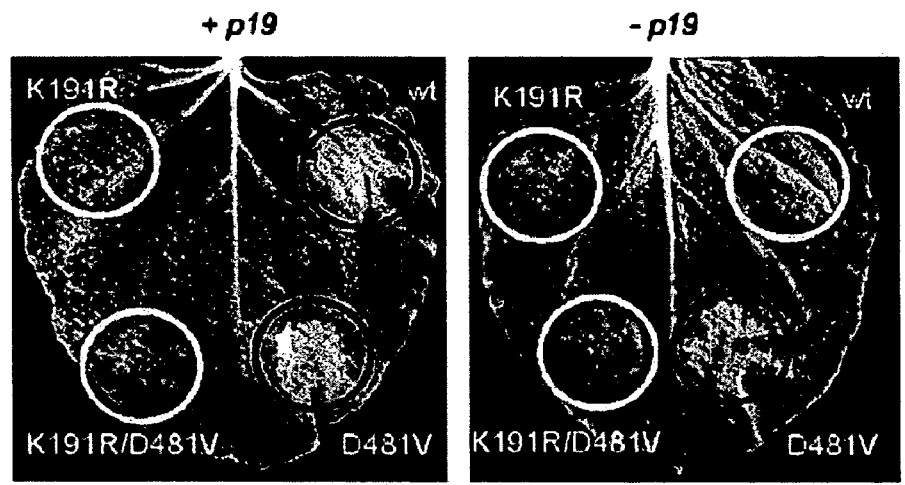

2.5 Transient Overexpression of NRC1 and Construction of a Constitutively Active NRC1 Protein To further investigate which genes are required for HR signaling by the CC-NB-LRR protein the effect of overexpression of NRC1 was investigated. Therefore, the coding sequence (SEQ ID NO: 1) of the cDNA was fused to the constitutive 35S promoter and inserted into a binary vector. Agroinfiltration of this construct in *N. benthamiana* did not result in an HR, whereas expression of a mix of NRC1 and the p19 silencing inhibitor (Voinnet et al., 2003, *Plant J.* 33, 949-956) did provoke an elicitor-independent HR (FIG. 4B). Agroinfiltration of a construct encoding a P-loop mutant of NRC1 (K191R) disrupting the P-loop motif, thereby affecting ATP hydrolysis (Tameling et al., 2002, *Plant Cell* 14, 2929-2939), either with or without p19, did not result in an HR (FIG. 4B).

The above described data indicated that post transcriptional gene silencing (PTGS) of the NRC1 gene may, therefore, prevent the development of an HR in NRC1 overexpressing tissue. Also, the disruption of the P-loop motif results in a non-functional NRC1 protein.

Since mutations in the MHD motif of the NB-LRR resistance proteins Rx (D460V) (Bendahmane et al., 2002; Tameling et al., 2002) and I-2 (D495V) (Bendahmane et al., 2002, *Plant J.* 32, 195-204; Tameling et al., 2002, *Plant Cell* 14, 2929-2939; Van Bentem et al., 2005, *Plant J.* 43, 284-298) result in constitutive activity, the inventors generated a similar mutant of NRC1 (NRC1$^{D481V}$). Indeed, agroinfiltration of NRC1$^{D481V}$ resulted in an elicitor-independent HR in leaves of *N. benthamiana* within three days post infiltration and again no HR was observed upon agroinfiltration of the double mutant NRC1$^{K191R/D481V}$ (FIG. 4B). Furthermore, no HR was induced upon expression of NRC1$^{D481V}$ in SGT1-silenced plants (see below). These results indicate that the response induced upon agroinfiltration of NRC1$^{D481V}$ is specifically due to constitutive activity of the NRC1 protein and that NRC1 functions in a signal transduction cascade leading to HR.

2.6 Epistatis Experiments Using a Constitutively Active NCR1 Protein

Epistasis experiments employing NRC1$^{D481V}$ were performed to further investigate which genes are required for HR signaling by this protein, and thereby determine its putative position in an HR pathway. In addition to VIGS of genes known to be generally involved in HR signaling, such as SGT1 and RAR1 (Required for Mla12 resistance) (Shirasu and Schulze-Lefert, 2003, *Trends Plant Sci.* 8, 252-258), *N. benthamiana*:Cf-4 was silenced for NDR1 (non race-specific disease resistance) (Century et al., 1995, *Proc. Natl. Acad. Sci. USA* 92, 6597-6601), EDS1 (enhanced disease susceptibility) (Aarts et al., 1998, *Proc. Natl. Acad. Sci. USA* 95, 10306-10311) and MEK2 (a MAPKK) (Ekengren et al., 2003, *Plant J.* 36, 905-917), and subsequently agroinfiltrated with NRC1$^{D481V}$ or Avr4. Furthermore, VIGS using TRV:00, TRV:Cf-4 and TRV:NRC1 was included as controls. A compromised NRC1$^{D481V}$- or Avr4-induced HR indicates 'knock-down' of a gene required for respectively NRC1- or Cf-4/Avr4-induced HR signaling.

Figure 4C:
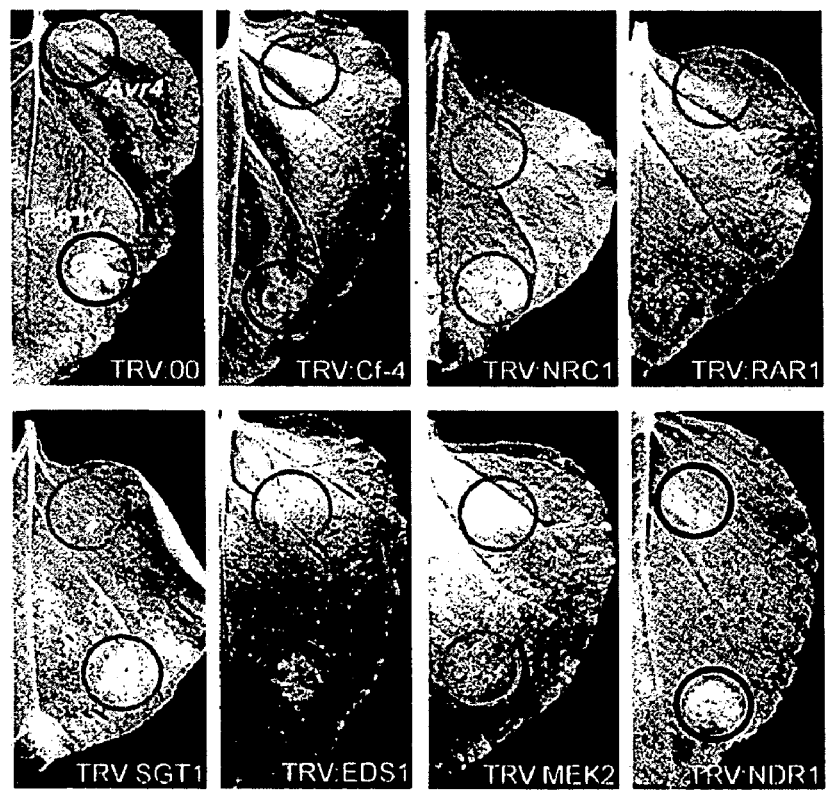

As expected, HR induced upon agroinfiltration of Avr4 was compromised in TRV:Cf-4- and TRV:NRC1-infected plants. Cf-4-mediated signaling also requires EDS1, as plants silenced for this gene displayed a less severe Avr4-induced HR. In addition, the inventors found a reduced HR upon agroinfiltration of Avr4 in plants silenced for MEK2, RAR1 and SGT1 (FIG. 4C; light circles). The Avr4-induced HR is not compromised in TRV:00- and TRV:NDR1-infected plants (FIG. 4C; dark circles), indicating that NDR1 is not required for Cf-4-mediated signaling. Similarly, NRC1$^{D481V}$-induced HR was not compromised in TRV:00- and TRV:NDR1-infected plants, and also not in TRV:Cf-4-infected plants. Interestingly, in contrast to Avr4, NRC1$^{D481V}$ still induces an HR in TRV:EDS1-infected plants, indicating that NRC1 is functional downstream of EDS1 (FIG. 4C; dark circles). The NRC1$^{D481V}$-induced HR is compromised in plants silenced for MEK2, showing that NRC1 requires the MAP kinase cascade for its signaling and can be positioned upstream of these kinases. VIGS of RAR1 and SGT1 also compromises D481V-induced HR, similar to the HR induced by Avr4 (FIG. 4C; light circles). Thus, NRC1 is required for HR signaling initiated by Cf-4 and can be positioned upstream of the MAPK cascade and downstream of EDS1.

See FIG. 5 for a model of NRC1 mediated cell signaling.

Example 3

NRC1 Requirement for Mi-Mediated Resistance

In order to determine whether NRC1 is required for Mi-mediated resistance against nematodes, white fly and aphids, a constitutively active form of Mi (see U.S. Pat. No. 6,613,962 and EP0937155B1) is agroinfiltrated into NRC1 silenced plants. A decreased HR in NRC1 silenced plants indicates that NRC1 is also required for Mi-mediated HR and that (over)expression of NRC1 can be used to generate transgenic plants having enhanced resistance against nematodes, white fly and aphids.

The above example is provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. A method for producing a transgenic plant having enhanced disease resistance compared to a non-transgenic control plant, said method comprising the steps of:

a) transforming a plant or plant cell with a nucleotide sequence encoding a protein comprising an amino acid sequence at least 95% identical to SEQ ID NO:2, wherein the nucleotide sequence is operably linked to a promoter active in plant cells, b) regenerating a plant, wherein the regenerated plant has enhanced disease resistance compared to a non-transgenic control plant.

2. The method according to claim 1, wherein said nucleotide sequence is integrated into the genome of said plant.

3. The method according to claim 1, further comprising
c) screening the regenerated plant, or a plant derived therefrom by selfing or crossing, for resistance to one or more plant pathogens and identifying a plant comprising enhanced resistance to one or more of said plant pathogens.

4. The method according to claim 1, wherein said promoter is a pathogen inducible promoter.

5. The method according to claim 1, wherein the protein comprises the amino acid sequence of SEQ ID NO: 2.

6. The method according to claim 1, wherein the plant belongs to the family Solanaceae.

7. The method according to claim 6, wherein the plant is of the genus *Solanum*.

8. A transgenic plant, plant cell, seed or fruit, obtainable by the method according to claim 1.

9. A plant, plant cell, seed or fruit comprising a chimeric gene, the chimeric gene comprising a promoter active in plant cells operably linked to a nucleic acid encoding a protein comprising an amino acid sequence at least 95% identical to SEQ ID NO:2.

10. The plant of claim 9, wherein the plant is of the genus *Solanum*.

11. The method according to claim 1, wherein the protein comprises the amino acid sequence of SEQ ID NO:4.

12. The plant, plant cell, seed or fruit of claim 9, wherein the protein comprises the amino acid sequence of SEQ ID NO: 2.

13. The plant, plant cell, seed or fruit of claim 9, wherein the protein comprises the amino acid sequence of SEQ ID NO: 4.

14. A plant of claim 9.

15. A plant cell of claim 9.

16. A seed of claim 9.

17. A fruit of claim 9.

18. The plant, plant cell, seed or fruit of claim 9, wherein the plant belongs to the family Solanaceae.

* * * * *

SEQUENCE LISTING

```
<160> NUMBER OF SEQ ID NOS: 5

<210> SEQ ID NO 1
<211> LENGTH: 2664
<212> TYPE: DNA
<213> ORGANISM: Unknown
<220> FEATURE:
<223> OTHER INFORMATION: Tomato nrc1 open reading frame

<400> SEQUENCE: 1
atggttgatg tagggttga atttctgtta gagaacttga agcaattggt actggacaat      60
gtggagttaa tcggaggagc taaagatgaa atcgagaatc tgcgtgatga tttgagtgaa     120
ttcaatgcct ttctcaagca agctgcaatg gtccgcagcg aaaacccagt tctcaaagaa     180
ctagtgagga gtatcagaaa agtggtgaat cgtgctgaag atgctgttga taaatttgta     240
attgaagcta aagttcataa agacaaaggg tttaaagggg ttttcgataa acctggacat     300
tatagaagag tgagggatgc agctgtggag attaaaggta tcagagataa aatgagagaa     360
attcggcaaa ataaggcaca tggccttcag gctctacttc aagatcatga tgattcaatc     420
agcagaggtg gagaagagag acagcctcct gtggttgagg aagatgatgt ggtgggcttt     480
gacgatgagg cgcagacggt aatcgaccgt cttcttgaag gatcaggtga tttagaggtt     540
attccagtag ttggaatgcc tggtcttggc aaaactacac tagccactaa gatcttcaag     600
catccgaaga ttgagtacga gttctttact agactttggc tttacgtttc ccaatcatac     660
aagacaagag aattatatct taacatcatc agtaaattca ccggaaacac caaacattgc     720
cgtgatatgt ctgaaaagga tttagctctt aaggtacaag agattttgga agaaggagga     780
aaatacttga ttgtcttgga tgatgtctgg tcgacagatg cttgggatcg tatcaagatt     840
gctttcccga aaaatgacaa gggcaataga gtattgttga ctactcgaga ccaccgtgtt     900
gcaagatatt gcaataggag tccacatgat ttaaaatttc tgactgatga agagagttgg     960
attttactgg agaaaagagc ttttcacaaa gctaaatgtc tccccgaatt ggaaacaaac    1020
ggaaaaagca tagccaggaa gtgtaaagga ctaccccttg ctattgtggt gattgcagga    1080
gctctaattg ggaaaagcaa aacaataaag gaatgggagc aagtggatca gagtgtgggc    1140
gaacatttca taaatagaga tcagccaaat agttgtgata aattggtacg gatgagttat    1200
gatgttttgc cttatgactg gaaagcttgc tttttatact tcggtacatt ccccagaggc    1260
tatttaatcc ctgccaggaa attgatccgc ttatggatcg cggaagggtt tatccagtac    1320
agaggggact tatcccctga gtgtaaagca gaggagtact tgaatgaact cgtaaataga    1380
aacttagtga tggtaatgca aggacggtt gatggacaaa tcaaaacttg tcgtgttcat    1440
```

-continued

```
gacatgttgt atgagttttg ctggcaagag gctacgacag aggaaaatct tttccatgaa    1500
gtaaaattcg gtggtgagca atctgttcgt gaagtatcca ctcatcgtcg cttgtgcatt    1560
cattcctctg ttgtggagtt catttctaag aagccctctg gtgagcatgt taggtcgttc    1620
ctatgttttt ctccagaaaa aattgacact cccccaactg tcagtgcaaa catatcaaaa    1680
gcctttccat tgctaagggt gtttgatact gaatccatca aaatcaatcg cttttgcaag    1740
gagttctttc aattgtatca tctgaggtat attgctttct catttgactc gattaaagtc    1800
attccgaaac atgttgggga actttggaac gtacaaaccc tcattgtcaa cacacaacag    1860
atcaaccttg atattcaagc agacatattg aacatgcccc ggctgaggca tctgctcacc    1920
aacacgtctg ctaaattgcc tgcgcttgct aaccccaaaa caagtaagac taccttggta    1980
aatcaaagcc tgcaaaccct ctccacaatt gcaccgaaaa gctgcactga gtatgttctc    2040
tcgagggctc caaacttgaa aaactgggc attcgtggaa aaatagctaa gctaatggaa    2100
ccaagtcagt ctgtattgtt gaacaatgtt aagaggctgc aatttcttga aacttgaag    2160
ctgataaatg ttggtcagat tgatcagaca caattacgcc ttcctccagc atctatattt    2220
ccaacaaagt tgaggaagct gactttatta gatacctggt tggagtggga tgatatgtct    2280
gtattgaaac agctggagaa ccttcaagtc ttgaagctga aggacaatgc atttaaggga    2340
gagaactggg aactaaatga tggaggtttt cctttcctac aagtgttatg cattgaaagg    2400
gcaaacttag tttcttggaa tgcttcaggt gatcacttcc cgagacttaa acatcttcac    2460
atatcatgtg ataaacttga gaagatcccc attggcctgg ctgatatatg cagcctccaa    2520
gtgatggatt tgcgaaattc cactaaatca gcagcaaaat ctgccagaga gatacaagcc    2580
aaaaaaaaca agctgcaacc tgctaaatcc cagaagttcg agctttctgt attccctcct    2640
gattctgatg tacagacagc ttct                                            2664
```

<210> SEQ ID NO 2
<211> LENGTH: 888
<212> TYPE: PRT
<213> ORGANISM: Unknown
<220> FEATURE:
<223> OTHER INFORMATION: Tomato NRC1 wild type protein

<400> SEQUENCE: 2

```
Met Val Asp Val Gly Val Glu Phe Leu Leu Glu Asn Leu Lys Gln Leu
 1               5                  10                  15

Val Leu Asp Asn Val Glu Leu Ile Gly Gly Ala Lys Asp Glu Ile Glu
            20                  25                  30

Asn Leu Arg Asp Asp Leu Ser Glu Phe Asn Ala Phe Leu Lys Gln Ala
        35                  40                  45

Ala Met Val Arg Ser Glu Asn Pro Val Leu Lys Glu Leu Val Arg Ser
    50                  55                  60

Ile Arg Lys Val Val Asn Arg Ala Glu Asp Ala Val Asp Lys Phe Val
65                  70                  75                  80

Ile Glu Ala Lys Val His Lys Asp Lys Gly Phe Lys Gly Val Phe Asp
                85                  90                  95

Lys Pro Gly His Tyr Arg Arg Val Arg Asp Ala Ala Val Glu Ile Lys
            100                 105                 110

Gly Ile Arg Asp Lys Met Arg Glu Ile Arg Gln Asn Lys Ala His Gly
        115                 120                 125

Leu Gln Ala Leu Leu Gln Asp His Asp Asp Ser Ile Ser Arg Gly Gly
    130                 135                 140
```

-continued

```
Glu Glu Arg Gln Pro Pro Val Glu Glu Asp Val Val Gly Phe
145                 150                 155                 160

Asp Asp Glu Ala Gln Thr Val Ile Asp Arg Leu Leu Glu Gly Ser Gly
                165                 170                 175

Asp Leu Glu Val Ile Pro Val Val Gly Met Pro Gly Leu Gly Lys Thr
                180                 185                 190

Thr Leu Ala Thr Lys Ile Phe Lys His Pro Lys Ile Glu Tyr Glu Phe
                195                 200                 205

Phe Thr Arg Leu Trp Leu Tyr Val Ser Gln Ser Tyr Lys Thr Arg Glu
            210                 215                 220

Leu Tyr Leu Asn Ile Ile Ser Lys Phe Thr Gly Asn Thr Lys His Cys
225                 230                 235                 240

Arg Asp Met Ser Glu Lys Asp Leu Ala Leu Lys Val Gln Glu Ile Leu
                245                 250                 255

Glu Glu Gly Gly Lys Tyr Leu Ile Val Leu Asp Asp Val Trp Ser Thr
                260                 265                 270

Asp Ala Trp Asp Arg Ile Lys Ile Ala Phe Pro Lys Asn Asp Lys Gly
            275                 280                 285

Asn Arg Val Leu Leu Thr Thr Arg Asp His Arg Val Ala Arg Tyr Cys
290                 295                 300

Asn Arg Ser Pro His Asp Leu Lys Phe Leu Thr Asp Glu Ser Trp
305                 310                 315                 320

Ile Leu Leu Glu Lys Arg Ala Phe His Lys Ala Lys Cys Leu Pro Glu
                325                 330                 335

Leu Glu Thr Asn Gly Lys Ser Ile Ala Arg Lys Cys Lys Gly Leu Pro
            340                 345                 350

Leu Ala Ile Val Val Ile Ala Gly Ala Leu Ile Gly Lys Ser Lys Thr
            355                 360                 365

Ile Lys Glu Trp Glu Gln Val Asp Gln Ser Val Gly Glu His Phe Ile
370                 375                 380

Asn Arg Asp Gln Pro Asn Ser Cys Asp Lys Leu Val Arg Met Ser Tyr
385                 390                 395                 400

Asp Val Leu Pro Tyr Asp Trp Lys Ala Cys Phe Leu Tyr Phe Gly Thr
                405                 410                 415

Phe Pro Arg Gly Tyr Leu Ile Pro Ala Arg Lys Leu Ile Arg Leu Trp
            420                 425                 430

Ile Ala Glu Gly Phe Ile Gln Tyr Arg Gly Asp Leu Ser Pro Glu Cys
            435                 440                 445

Lys Ala Glu Glu Tyr Leu Asn Glu Leu Val Asn Arg Asn Leu Val Met
    450                 455                 460

Val Met Gln Arg Thr Val Asp Gly Gln Ile Lys Thr Cys Arg Val His
465                 470                 475                 480

Asp Met Leu Tyr Glu Phe Cys Trp Gln Glu Ala Thr Thr Glu Asn
                485                 490                 495

Leu Phe His Glu Val Lys Phe Gly Gly Glu Gln Ser Val Arg Glu Val
                500                 505                 510

Ser Thr His Arg Arg Leu Cys Ile His Ser Ser Val Val Glu Phe Ile
            515                 520                 525

Ser Lys Lys Pro Ser Gly Glu His Val Arg Ser Phe Leu Cys Phe Ser
    530                 535                 540

Pro Glu Lys Ile Asp Thr Pro Thr Val Ser Ala Asn Ile Ser Lys
545                 550                 555                 560

Ala Phe Pro Leu Leu Arg Val Phe Asp Thr Glu Ser Ile Lys Ile Asn
```

-continued

```
                565                 570                 575
Arg Phe Cys Lys Glu Phe Phe Gln Leu Tyr His Leu Arg Tyr Ile Ala
            580                 585                 590
Phe Ser Phe Asp Ser Ile Lys Val Ile Pro Lys His Val Gly Glu Leu
        595                 600                 605
Trp Asn Val Gln Thr Leu Ile Val Asn Thr Gln Gln Ile Asn Leu Asp
    610                 615                 620
Ile Gln Ala Asp Ile Leu Asn Met Pro Arg Leu Arg His Leu Leu Thr
625                 630                 635                 640
Asn Thr Ser Ala Lys Leu Pro Ala Leu Ala Asn Pro Lys Thr Ser Lys
            645                 650                 655
Thr Thr Leu Val Asn Gln Ser Leu Gln Thr Leu Ser Thr Ile Ala Pro
        660                 665                 670
Glu Ser Cys Thr Glu Tyr Val Leu Ser Arg Ala Pro Asn Leu Lys Lys
    675                 680                 685
Leu Gly Ile Arg Gly Lys Ile Ala Lys Leu Met Glu Pro Ser Gln Ser
690                 695                 700
Val Leu Leu Asn Val Lys Arg Leu Gln Phe Leu Glu Asn Leu Lys
705                 710                 715                 720
Leu Ile Asn Val Gly Gln Ile Asp Gln Thr Gln Leu Arg Leu Pro Pro
            725                 730                 735
Ala Ser Ile Phe Pro Thr Lys Leu Arg Lys Leu Thr Leu Leu Asp Thr
        740                 745                 750
Trp Leu Glu Trp Asp Asp Met Ser Val Leu Lys Gln Leu Glu Asn Leu
    755                 760                 765
Gln Val Leu Lys Leu Lys Asp Asn Ala Phe Lys Gly Glu Asn Trp Glu
770                 775                 780
Leu Asn Asp Gly Gly Phe Pro Phe Leu Gln Val Leu Cys Ile Glu Arg
785                 790                 795                 800
Ala Asn Leu Val Ser Trp Asn Ala Ser Gly Asp His Phe Pro Arg Leu
            805                 810                 815
Lys His Leu His Ile Ser Cys Asp Lys Leu Glu Lys Ile Pro Ile Gly
        820                 825                 830
Leu Ala Asp Ile Cys Ser Leu Gln Val Met Asp Leu Arg Asn Ser Thr
    835                 840                 845
Lys Ser Ala Ala Lys Ser Ala Arg Glu Ile Gln Ala Lys Lys Asn Lys
850                 855                 860
Leu Gln Pro Ala Lys Ser Gln Lys Phe Glu Leu Ser Val Phe Pro Pro
865                 870                 875                 880
Asp Ser Asp Val Gln Thr Ala Ser
            885
```

<210> SEQ ID NO 3
<211> LENGTH: 3168
<212> TYPE: DNA
<213> ORGANISM: Unknown
<220> FEATURE:
<223> OTHER INFORMATION: Tomato nrc1 full length cDNA

<400> SEQUENCE: 3

| | | | | |
|---|---|---|---|---|
| gaattcggca cgaggcttct tctgagcata attctcttct tctccaagaa atcaatcgaa | | | | 60 |
| aaaaaaaaaa aaaggaaaac aatatggttg atgtaggggt tgaatttctg ttagagaact | | | | 120 |
| tgaagcaatt ggtactggac aatgtggagt taatcggagg agctaaagat gaaatcgaga | | | | 180 |
| atctgcgtga tgatttgagt gaattcaatg cctttctcaa gcaagctgca atggtccgca | | | | 240 |

-continued

```
gcgaaaaccc agttctcaaa gaactagtga ggagtatcag aaaagtggtg aatcgtgctg    300
aagatgctgt tgataaattt gtaattgaag ctaaagttca taaagacaaa gggtttaaag    360
gggttttcga taaacctgga cattatagaa gagtgaggga tgcagctgtg gagattaaag    420
gtatcagaga taaaatgaga gaaattcggc aaaataaggc acatggcctt caggctctac    480
ttcaagatca tgatgattca atcagcagag gtggagaaga gagacagcct cctgtggttg    540
aggaagatga tgtggtgggc tttgacgatg aggcgcagac ggtaatcgac cgtcttcttg    600
aaggatcagg tgatttagag gttattccag tagttggaat gcctggtctt ggcaaaacta    660
cactagccac taagatcttc aagcatccga agattgagta cgagttcttt actagacttt    720
ggctttacgt ttcccaatca tacaagacaa gagaattata tcttaacatc atcagtaaat    780
tcaccggaaa caccaaacat tgccgtgata tgtctgaaaa ggatttagct cttaaggtac    840
aagagatttt ggaagaagga ggaaaatact tgattgtctt ggatgatgtc tggtcgacag    900
atgcttggga tcgtatcaag attgctttcc cgaaaaatga caagggcaat agagtattgt    960
tgactactcg agaccaccgt gttgcaagat attgcaatag gagtccacat gatttaaaat    1020
ttctgactga tgaagagagt tggatttttac tggagaaaag agcttttcac aaagctaaat    1080
gtctccccga attggaaaca aacgaaaaaa gcatagccag gaagtgtaaa ggactacccc    1140
ttgctattgt ggtgattgca ggagctctaa ttgggaaaag caaaacaata aaggaatggg    1200
agcaagtgga tcagagtgtg ggcgaacatt tcataaatag agatcagcca aatagttgtg    1260 ataaaattggt acgatgagt tatgatgttt tgccttatga ctggaaagct tgcttttat    1320 acttcggtac attccccaga ggctatttaa tccctgccag gaaattgatc cgcttatgga    1380
tcgcggaagg gtttatccag tacagagggg acttatcccc tgagtgtaaa gcagaggagt    1440
acttgaatga actcgtaaat agaaacttag tgatggtaat gcaaaggacg gttgatggac    1500
aaaatcaaac ttgtcgtgtt catgacatgt tgtatgagtt tgctggcaa gaggctacga    1560 cagaggaaaa tcttttccat gaagtaaaat tcggtggtga gcaatctgtt cgtgaagtat    1620
ccactcatcg tcgcttgtgc attcattcct ctgttgtgga gttcatttct aagaagccct    1680
ctggtgagca tgttaggtcg ttcctatgtt tttctccaga aaaaattgac actcccccaa    1740
ctgtcagtgc aaacatatca aaagcctttc cattgctaag ggtgtttgat actgaatcca    1800
tcaaaatcaa tcgcttttgc aaggagttct ttcaattgta tcatctgagg tatattgctt    1860
tctcatttga ctcgattaaa gtcattccga aacatgttgg ggaactttgg aacgtacaaa    1920
ccctcattgt caacacacaa cagatcaacc ttgatattca agcagacata ttgaacatgc    1980
cccggctgag gcatctgctc accaacacgt ctgctaaatt gcctgcgctt gctaacccca    2040
aaacaagtaa gactaccttg gtaaatcaaa gcctgcaaac cctctccaca attgcaccag    2100
aaagctgcac tgagtatgtt ctctcgaggg ctccaaactt gaaaaaactg ggcattcgtg    2160
gaaaaatagc taagctaatg gaaccaagtc agtctgtatt gttgaacaat gttaagaggc    2220
tgcaatttct tgagaacttg aagctgataa atgttggtca gattgatcag acacaattac    2280
gccttcctcc agcatctata tttccaacaa agttgaggaa gctgactta ttagataccl    2340 ggttggagtg ggatgatatg tctgtattga acagctggaa gaaccttcaa gtcttgaagc    2400
tgaaggacaa tgcatttaag ggagagaact gggaactaaa tgatggaggt tttccttcc    2460 tacaagtgtt atgcattgaa agggcaaact tagtttcttg gaatgcttca ggtgatcact    2520
tcccgagact taaacatctt cacatatcat gtgataaact tgagaagatc cccattggcc    2580
```

-continued

```
tggctgatat atgcagcctc caagtgatgg atttgcgaaa ttccactaaa tcagcagcaa    2640
aatctgccag agagatacaa gccaaaaaaa acaagctgca acctgctaaa tcccagaagt    2700
tcgagctttc tgtattccct cctgattctg atgtacagac agcttcttag aaaggtctaa    2760
aataaccaca tgctgcaggt tcaaccagcc tggttggcgc gcatggtttt tgcttcattt    2820
ggatcactgc tttcacagtg aaacctattg catttcataa gtggaacgac tgatccacgg    2880
ttttgcaact ctttggtttc ttactgtatt tgatgtgagt tcatgtttta ttgattgtgg    2940
atgcaatgtg tcatcatagc caaggaataa gaaccaaatg taacgttcaa gaaatatcag    3000
acattgtttc ttataagtta taccactctg aattttctcc ttttagatac aacagcagaa    3060
caagtcactt gttttgattc atacacaatt tgatcatgtg ttattattta aacagcactt    3120
ttggtaaaaa aaaaaaaaaa aaaaaaaaaa aaaaaaaaa aactcgag                   3168
```

<210> SEQ ID NO 4
<211> LENGTH: 888
<212> TYPE: PRT
<213> ORGANISM: Unknown
<220> FEATURE:
<223> OTHER INFORMATION: constitutive NRC1 protein (D481V mutant)

<400> SEQUENCE: 4

```
Met Val Asp Val Gly Val Glu Phe Leu Leu Glu Asn Leu Lys Gln Leu
  1               5                  10                  15

Val Leu Asp Asn Val Glu Leu Ile Gly Gly Ala Lys Asp Glu Ile Glu
                 20                  25                  30

Asn Leu Arg Asp Asp Leu Ser Glu Phe Asn Ala Phe Leu Lys Gln Ala
             35                  40                  45

Ala Met Val Arg Ser Glu Asn Pro Val Leu Lys Glu Leu Val Arg Ser
         50                  55                  60

Ile Arg Lys Val Val Asn Arg Ala Glu Asp Ala Val Asp Lys Phe Val
 65                  70                  75                  80

Ile Glu Ala Lys Val His Lys Asp Lys Gly Phe Lys Gly Val Phe Asp
                 85                  90                  95

Lys Pro Gly His Tyr Arg Arg Val Arg Asp Ala Ala Val Glu Ile Lys
            100                 105                 110

Gly Ile Arg Asp Lys Met Arg Glu Ile Arg Gln Asn Lys Ala His Gly
        115                 120                 125

Leu Gln Ala Leu Leu Gln Asp His Asp Asp Ser Ile Ser Arg Gly Gly
    130                 135                 140

Glu Glu Arg Gln Pro Pro Val Val Glu Asp Val Val Gly Phe
145                 150                 155                 160

Asp Asp Glu Ala Gln Thr Val Ile Asp Arg Leu Leu Glu Gly Ser Gly
                165                 170                 175

Asp Leu Glu Val Ile Pro Val Val Gly Met Pro Gly Leu Gly Lys Thr
            180                 185                 190

Thr Leu Ala Thr Lys Ile Phe Lys His Pro Lys Ile Glu Tyr Glu Phe
        195                 200                 205

Phe Thr Arg Leu Trp Leu Tyr Val Ser Gln Ser Tyr Lys Thr Arg Glu
    210                 215                 220

Leu Tyr Leu Asn Ile Ile Ser Lys Phe Thr Gly Asn Thr Lys His Cys
225                 230                 235                 240

Arg Asp Met Ser Glu Lys Asp Leu Ala Leu Lys Val Gln Glu Ile Leu
                245                 250                 255

Glu Glu Gly Gly Lys Tyr Leu Ile Val Leu Asp Asp Val Trp Ser Thr
```

```
                260                 265                 270
Asp Ala Trp Asp Arg Ile Lys Ile Ala Phe Pro Lys Asn Asp Lys Gly
            275                 280                 285
Asn Arg Val Leu Leu Thr Thr Arg Asp His Arg Val Ala Arg Tyr Cys
            290                 295                 300
Asn Arg Ser Pro His Asp Leu Lys Phe Leu Thr Asp Glu Glu Ser Trp
305                 310                 315                 320
Ile Leu Leu Glu Lys Arg Ala Phe His Lys Ala Lys Cys Leu Pro Glu
                325                 330                 335
Leu Glu Thr Asn Gly Lys Ser Ile Ala Arg Lys Cys Lys Gly Leu Pro
            340                 345                 350
Leu Ala Ile Val Val Ile Ala Gly Ala Leu Ile Gly Lys Ser Lys Thr
            355                 360                 365
Ile Lys Glu Trp Glu Gln Val Asp Gln Ser Val Gly Glu His Phe Ile
370                 375                 380
Asn Arg Asp Gln Pro Asn Ser Cys Asp Lys Leu Val Arg Met Ser Tyr
385                 390                 395                 400
Asp Val Leu Pro Tyr Asp Trp Lys Ala Cys Phe Leu Tyr Phe Gly Thr
                405                 410                 415
Phe Pro Arg Gly Tyr Leu Ile Pro Ala Arg Lys Leu Ile Arg Leu Trp
            420                 425                 430
Ile Ala Glu Gly Phe Ile Gln Tyr Arg Gly Asp Leu Ser Pro Glu Cys
            435                 440                 445
Lys Ala Glu Glu Tyr Leu Asn Glu Leu Val Asn Arg Asn Leu Val Met
450                 455                 460
Val Met Gln Arg Thr Val Asp Gly Gln Ile Lys Thr Cys Arg Val His
465                 470                 475                 480
Val Met Leu Tyr Glu Phe Cys Trp Gln Glu Ala Thr Glu Glu Asn
                485                 490                 495
Leu Phe His Glu Val Lys Phe Gly Gly Glu Gln Ser Val Arg Glu Val
            500                 505                 510
Ser Thr His Arg Arg Leu Cys Ile His Ser Ser Val Val Glu Phe Ile
            515                 520                 525
Ser Lys Lys Pro Ser Gly Glu His Val Arg Ser Phe Leu Cys Phe Ser
            530                 535                 540
Pro Glu Lys Ile Asp Thr Pro Thr Val Ser Ala Asn Ile Ser Lys
545                 550                 555                 560
Ala Phe Pro Leu Leu Arg Val Phe Asp Thr Glu Ser Ile Lys Ile Asn
                565                 570                 575
Arg Phe Cys Lys Glu Phe Phe Gln Leu Tyr His Leu Arg Tyr Ile Ala
            580                 585                 590
Phe Ser Phe Asp Ser Ile Lys Val Ile Pro Lys His Val Gly Glu Leu
            595                 600                 605
Trp Asn Val Gln Thr Leu Ile Val Asn Thr Gln Gln Ile Asn Leu Asp
            610                 615                 620
Ile Gln Ala Asp Ile Leu Asn Met Pro Arg Leu Arg His Leu Leu Thr
625                 630                 635                 640
Asn Thr Ser Ala Lys Leu Pro Ala Leu Ala Asn Pro Lys Thr Ser Lys
                645                 650                 655
Thr Thr Leu Val Asn Gln Ser Leu Gln Thr Leu Ser Thr Ile Ala Pro
            660                 665                 670
Glu Ser Cys Thr Glu Tyr Val Leu Ser Arg Ala Pro Asn Leu Lys Lys
            675                 680                 685
```

```
Leu Gly Ile Arg Gly Lys Ile Ala Lys Leu Met Glu Pro Ser Gln Ser
    690                 695                 700

Val Leu Leu Asn Asn Val Lys Arg Leu Gln Phe Leu Glu Asn Leu Lys
705                 710                 715                 720

Leu Ile Asn Val Gly Gln Ile Asp Gln Thr Gln Leu Arg Leu Pro Pro
                725                 730                 735

Ala Ser Ile Phe Pro Thr Lys Leu Arg Lys Leu Thr Leu Leu Asp Thr
            740                 745                 750

Trp Leu Glu Trp Asp Asp Met Ser Val Leu Lys Gln Leu Glu Asn Leu
        755                 760                 765

Gln Val Leu Lys Leu Lys Asp Asn Ala Phe Lys Gly Glu Asn Trp Glu
    770                 775                 780

Leu Asn Asp Gly Gly Phe Pro Phe Leu Gln Val Leu Cys Ile Glu Arg
785                 790                 795                 800

Ala Asn Leu Val Ser Trp Asn Ala Ser Gly Asp His Phe Pro Arg Leu
                805                 810                 815

Lys His Leu His Ile Ser Cys Asp Lys Leu Glu Lys Ile Pro Ile Gly
            820                 825                 830

Leu Ala Asp Ile Cys Ser Leu Gln Val Met Asp Leu Arg Asn Ser Thr
        835                 840                 845

Lys Ser Ala Ala Lys Ser Ala Arg Glu Ile Gln Ala Lys Lys Asn Lys
    850                 855                 860

Leu Gln Pro Ala Lys Ser Gln Lys Phe Glu Leu Ser Val Phe Pro Pro
865                 870                 875                 880

Asp Ser Asp Val Gln Thr Ala Ser
                885

<210> SEQ ID NO 5
<211> LENGTH: 421
<212> TYPE: DNA
<213> ORGANISM: Unknown
<220> FEATURE:
<223> OTHER INFORMATION: 3'UTR of the tomato nrc1 gene

<400> SEQUENCE: 5
tagaaaggtc taaaataacc acatgctgca ggttcaacca gcctggttgg cgcgcatggt      60
ttttgcttca tttggatcac tgctttcaca gtgaaaccta ttgcatttca taagtggaac    120
gactgatcca cggttttgca actctttggt ttcttactgt atttgatgtg agttcatgtt    180
ttattgattg tggatgcaat gtgtcatcat agccaaggaa taagaaccaa atgtaacgtt    240
caagaaatat cagacattgt ttcttataag ttataccact ctgaattttc tccttttaga    300
tacaacagca gaacaagtca cttgttttga ttcatacaca atttgatcat gtgttattat    360
ttaaacagca cttttggtaa aaaaaaaaaa aaaaaaaaa  aaaaaaaaa  aaaaactcga    420 g                                                                    421
```